United States Patent
Shudo

(10) Patent No.: US 6,476,017 B2
(45) Date of Patent: *Nov. 5, 2002

(54) COMPOUNDS ACTIVATING PHARMACOLOGICAL EFFECT OF RETINOIDS

(75) Inventor: Koichi Shudo, Tokyo (JP)

(73) Assignee: Institute of Medicinal Molecular Design, Inc., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/838,272

(22) Filed: Apr. 20, 2001

(65) Prior Publication Data

US 2001/0039272 A1 Nov. 8, 2001

Related U.S. Application Data

(60) Continuation of application No. 09/626,449, filed on Jul. 26, 2000, now abandoned, which is a division of application No. 09/288,618, filed on Apr. 9, 1999, now Pat. No. 6,121,256, which is a division of application No. 08/710,657, filed on Sep. 20, 1996, now Pat. No. 5,929,069.

(30) Foreign Application Priority Data

Sep. 21, 1995 (JP) .................................. 7-242639
Jun. 12, 1996 (JP) .................................. 8-150582

(51) Int. Cl.[7] ...................... A61K 31/55; C07D 267/02; C07D 281/08
(52) U.S. Cl. ..................... 514/211.09; 514/211.11; 540/546; 540/547
(58) Field of Search ................... 540/546, 547; 514/211.09, 211.11

(56) References Cited

U.S. PATENT DOCUMENTS 5,344,828 A * 9/1994 Sawanishi et al. .......... 514/211

OTHER PUBLICATIONS

Chemical & Pharmaceutical Bulletin; vol. 43 (No. 10), p. 1827–1829 (Oct., 1995).
Journal of Medicinal Chemistry; vol. 37 (No. 10), p. 1508–1517 (May 13, 1994).
Journal of Organic Chemistry; vol. 37 (No. 24), p. 3755–3770 (1972) p. 3759 compound; 38a, 38b, preparation; p. 3568 (3768), right column.
Chemical Abstracts; vol. 66, p. 1046 (1967), Abstract No. 10838a, Abstract of Acta Chem. Scand., vol. 20 (No. 6) p. 1631–44 (1966).

* cited by examiner

Primary Examiner—Bruck Kifle
(74) Attorney, Agent, or Firm—Griffin & Szipl, P.C.

(57) ABSTRACT

A compound represented by the formula (I) or (II) or a salt thereof wherein $R^1$ represents hydrogen atom or a $C_{1-6}$ alkyl group; $R^2$ and $R^3$ independently represent a hydrogen atom or a $C_{1-6}$ alkyl group, or $R^2$ and $R^3$ may combine together to represent a 5- or 6-membered cycloalkyl group; $R^4$ represents, for example, a hydrogen atom or a $C_{1-6}$ alkyl group; $R^5$ represents, for example, a hydrogen atom or a $C_{1-6}$ alkyl group; $R^6$ represents a hydrogen atom or a $C_{1-6}$ alkyl group; X represents —$NR^7$—, —O—, —$CHR^7$— or —S— in which $R^7$ represents, for example, a hydrogen atom or a $C_{1-6}$ alkyl group; and Y represents a phenylene group or a pyridinediyl group. The compounds are useful as agents for enhancing the activities of retinoid compounds.

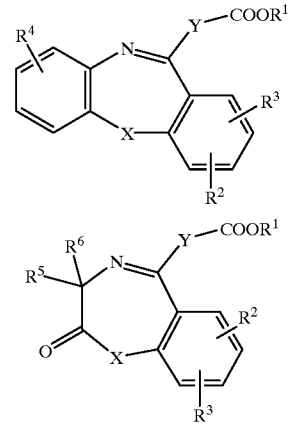

12 Claims, No Drawings

COMPOUNDS ACTIVATING PHARMACOLOGICAL EFFECT OF RETINOIDS

This application is a continuation of U.S. patent application Ser. No. 09/626,449, filed Jul. 26, 2000, now abandoned, which in turn is a division of U.S. patent application Ser. No. 09/288,618, filed Apr. 9, 1999, now U.S. Pat. No. 6,121,256, which in turn is a division of U.S. patent application Ser. No. 08/710,657, filed Sep. 20, 1996, now U.S. Pat. No. 5,929,069, issued Jul. 27, 1999, which claims priority based on Japanese Patent Application Nos. 242639/1995 and 150582/1996, filed Sep. 21, 1995 and Jun. 12, 1996, respectively. The entire disclosures of the above applications are hereby incorporated herein by reference.

TECHNICAL FIELD

The present invention relates to novel compounds, and it relates to novel compounds which enhance the physiological activity of the ligands to intranuclear receptors whose typical examples include retinoic acid and compounds having retinoic acid-like actions (retinoids).

BACKGROUND ART

Retinoic acid (vitamin A acid), an active metabolite of vitamin A, has extremely important physiological functions, e.g., differentiation of immature cells under development processes toward mature cells having specific functions, enhancement of cell proliferation, and life support action. It has been revealed that various vitamin A derivatives synthesized so far also have similar physiological functions, for example, the benzoic acid derivatives disclosed in Japanese Patent Unexamined Publication (KOKAI) Nos. (Sho)61-22047/1986 and (Sho)61-76440/1986 and the compounds described in Journal of Medicinal Chemistry, 1988, Vol. 31, No. 11, p.2182. "Retinoids" is a general term for retinoic acid and the aforementioned compounds having retinoic acid-like biological activities.

For example, it was proved that all-trans retinoic acid binds as a ligand to the retinoic acid receptor (RAR) present in cell nuclei, which belongs to the intranuclear receptor super family (Evans, R. M., Science, 240, p.889, 1988), and regulates proliferation and differentiation of animal cells or cellular mortalities (Petkovich, M., et al., Nature, 330, pp.444–450, 1987). It has also been suggested that the aforementioned compounds having the retinoic acid-like biological activities, e.g., 4-[(5,6,7,8-tetrahydro-5,5,8,8-tetramethyl-2-naphthalenyl)carbamoyl]benzoic acid: Am80, also bind to RAR in similar manners to retinoic acid to exhibit their physiological actions (see, Hashimoto, Y., Cell Struct. Funct., 16, pp.113–123, 1991; Hashimoto, Y., et al., Biochem. Biophys. Res. Commun., 166, pp.1300–1307, 1990). Clinically, these compounds were found as useful for the therapeutic and preventive treatment of vitamin A deficiency disease, hyperkeratosis of epithelial tissue, rheumatism, delayed allergy, bone disease, leukemia and certain types of cancer.

Compounds are known which antagonize against these retinoids and reduce the primary actions of the retinoid (Eyrolles, L., et al., Journal of Medicinal Chemistry, 37(10), pp.1508–1517, 1994). However, a compound has not been known, other than those disclosed in EP 694,301 A1, which enhances the actions of the retinoids such as retinoic acid, while the compound, per se, has no retinoid action or its retinoid actions are negligible. In this publication, it is suggested that a ligand compound specific to RXR receptor has an enhancing activity on Am80, i.e., a ligand specific to RAR-α-receptor.

SUMMARY OF THE INVENTION

An object of the present invention is to provide compounds having enhancing activities on the actions of the retinoids such as retinoic acid. More specifically, the object of the present invention is to provide compounds which can remarkably enhance the action of retinoids such as retinoic acid, while the compounds, per se, have no retinoid action or their retinoid actions are very weak.

The inventor of the present invention conducted various studies to achieve the foregoing object, and as a result, found that the compounds represented by the general formulas set out below enhance the action of retinoids such as retinoic acid. The present invention was achieved on the basis of the findings.

The present invention thus provides the compounds or the salts thereof represented by the following formula (I):

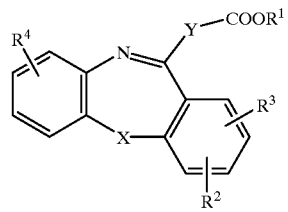

or the following formula (II):

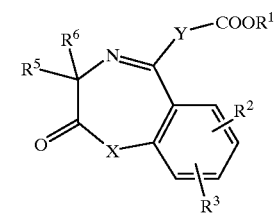

wherein, $R^1$ represents hydrogen atom or a $C_{1-6}$ alkyl group; $R^2$ and $R^3$ independently represent a hydrogen atom or a $C_{1-6}$ alkyl group, or $R^2$ and $R^3$ may combine together with the carbon atoms of the phenyl ring to which $R^2$ and $R^3$ bind to represent a 5- or 6-membered cycloalkyl group which may optionally be substituted with one or more $C_{1-4}$ alkyl groups; $R^4$ represents a hydrogen atom, a $C_{1-6}$ alkyl group, a $C_{1-6}$ alkoxy group, hydroxyl group, nitro group, or a halogen atom; $R^5$ represents a hydrogen atom, a $C_{1-6}$ alkyl group, or an aryl-substituted $C_{1-6}$ alkyl group; $R^6$ represents a hydrogen atom or a $C_{1-6}$ alkyl group; X represents —$NR^7$—, —O—, —$CHR^7$— or —S— in which $R^7$ represents a hydrogen atom, a $C_{1-6}$ alkyl group, or an aryl-substituted $C_{1-6}$ alkyl group; and Y represents a phenylene group or a pyridinediyl group. In addition, according to further embodiments of the present invention, there are provided a medicament comprising the aforementioned compounds; an agent enhancing the actions of the retinoid which comprises the aforementioned compounds; and an agent enhancing the actions of the ligands to the intranuclear receptors which comprises the aforementioned compounds.

THE MOST PREFERRED EMBODIMENTS TO CARRY OUT THE INVENTION

In the above general formula (I), $R^1$ represents a hydrogen atom or a linear or branched $C_{1-6}$ (i.e., having 1 to 6 carbon atoms) alkyl group. Examples of the alkyl group include, for example, methyl group, ethyl group, n-propyl group, isopropyl group, n-butyl group, sec-butyl group, and tert-butyl group, and methyl group is preferably used.

$R^2$ and $R^3$ independently represents a hydrogen atom or a linear or branched $C_{1-6}$ alkyl group. As for the alkyl group, those mentioned above may be used, and ethyl group, isopropyl group, tert-butyl group or the like may preferably be used. Each of $R^2$ and $R^3$ may independently substitute at any position and their substituting positions are not particularly limited. However, it is preferable that $R^2$ and $R^3$ are at para-position and meta-position with reference to X, respectively, $R^2$ and $R^3$ are at meta-position and ortho-position with reference to X. It is particularly preferable that $R^2$ and $R^3$ are at para-position and meta-position with reference to X, respectively.

$R^2$ and $R^3$ may combine to form a 5- or 6-membered cycloalkyl ring together with two carbon atoms on the phenyl ring to which $R^2$ and $R^3$ respectively bind. The cycloalkyl ring may have one or more $C_{1-4}$ alkyl groups. For example, the ring may have from two to four methyl groups, preferably four methyl groups. For example, it is preferable that $R^2$ and $R^3$ together with the phenyl ring substituted with $R^2$ and $R^3$ may form 5,6,7,8-tetrahydronaphthalene ring or 5,5,8,8-tetramethyl-5,6,7,8-tetrahydronaphthalene ring.

$R^4$ represents a hydrogen atom, a $C_{1-6}$ alkyl group, a $C_{1-6}$ alkoxy group, hydroxyl group, nitro group, or a halogen atom. As the $C_{1-6}$ alkyl group, these exemplified above may be used. As the $C_{1-6}$ alkoxy group, for example, methoxy group, ethoxy group, n-propoxy group, isopropoxy group, n-butoxy group, sec-butoxy group, or tert-butoxy group, preferably methoxy group, may be used. As the halogen atom, any of fluorine atom, chlorine atom, bromine atom, or iodine atom may be used. $R^4$ may substitute at any position on the phenyl ring and its position is not particularly limited.

$R^5$ represents a hydrogen atom, a $C_{1-6}$ alkyl group, or an aryl-substituted $C_{1-6}$ alkyl group. The $C_{1-6}$ alkyl group may be either linear or branched and those mentioned above may preferably be used. Examples of the aryl moiety of the aryl-substituted $C_{1-6}$ alkyl group include, for example, phenyl, naphthyl, or pyridyl group, and the $C_{1-6}$ alkyl moiety may be either linear or branched. For example, a phenyl-substituted $C_{1-6}$ alkyl group such as benzyl group or phenethyl group, a naphthyl-substituted $C_{1-6}$ alkyl group such as naphthylmethyl group, or a pyridyl-substituted $C_{1-6}$ alkyl group such as pyridylmethyl group can be used.

The aryl group constituting these aryl-substituted $C_{1-6}$ alkyl group may have one or more substituents. For example, a halogen atom such as fluorine atom or chlorine atom; a $C_{1-6}$ alkyl group such as methyl group or ethyl group; a linear or branched $C_{1-6}$ alkoxy group such as methoxy group or ethoxy group; nitro group; a linear or branched halogenated $C_{1-6}$ alkyl group such as trifluoromethyl group; hydroxyl group; carboxyl group; or a $C_{1-6}$ alkoxycarbonyl group such as methoxycarbonyl group or ethoxycarbonyl group may be used as the substituent. $R^6$ represents a hydrogen atom or a $C_{1-6}$ alkyl group. The $C_{1-6}$ alkyl group may be either linear or branched and those explained above may preferably used. The compound wherein both of $R^5$ and $R^6$ are hydrogen atoms, and the compound wherein $R^5$ is a $C_{1-6}$ alkyl group or an aryl-substituted $C_{1-6}$ alkyl group and $R^6$ is a hydrogen atom are particularly preferred compounds.

X represents a nitrogen atom substituted with $R^7$ (—$NR^7$—), an oxygen atom (—O—), a methylene group substituted with $R^7$ (—$CHR^7$—), or a sulfur atom (—S—). $R^7$ represents a hydrogen atom, a $C_{1-6}$ alkyl group, or an aryl-substituted $C_{1-6}$ alkyl group. The $C_{1-6}$ alkyl group may be either linear or branched and those exemplified above, e.g., methyl group, may be used. As the aryl-substituted $C_{1-6}$ alkyl group, those exemplified above, preferably benzyl group, may be used. The nitrogen atom and the sulfur atom may be in the form of N-oxide and sulfoxide, respectively. Among them, X may preferably be a nitrogen atom substituted with $R^7$ ($NR^7$), and X most preferably represents a nitrogen atom substituted with methyl group, ethyl group, n-propyl group, isopropyl group, or benzyl group.

Y represents a phenylene group or a pyridinediyl group. For example, any one of phenylene groups or pyridinediyl groups such as p-phenylene group, m-phenylene group, o-phenylene group, pyridine-2,4-diyl group, pyridine-2,5-diyl group, or pyridine-3,5-diyl group may be used. Preferably, p-phenylene group, m-phenylene group, or pyridine-2,5-diyl group may be used. Where pyridine-2,5-diyl group is used, the group represented by —$COOR^1$ may substitute either at 2-position or 5- position of the pyridine ring.

Acid addition salts and base addition salts fall within the scope of the compounds of the present invention. Examples of the acid addition salts include mineral acid salts such as hydrochloride or hydrobromide and organic acid salts such as p-toluenesulfonate, methanesulfonate, oxalate, or tartrate. The base addition salts may be formed where $R^1$ represents a hydrogen atom. Metal salts such as, for example, sodium salt, potassium salt, magnesium salt, or calcium salt, ammonium salts, or organic amine salts such as, for example, triethylamine salt or ethanolamine salt, for example, may be used.

As for the compounds of the present invention represented by formula (II), where $R^5$ and $R^6$ are different substituents to each other, the carbon atom substituted thereby is recognized as an asymmetric carbon. On the assumption that, in the formula (II), the 7-membered ring containing X forms a plane, either $R^5$ or $R^6$ may be above the plane. In addition, the compounds of the formula (I) and the formula (II) of the present invention may have one or more additional asymmetric carbons depending on the sorts of X and other substituents. Any optical isomers based on one or more of such asymmetric carbons, any mixture of optical isomers, racemates, any diastereomers based on two or more asymmetric carbons, any mixtures of the diastereomers and the like fall within the scope of the present invention. It should also be understood that any hydrates or solvates of the compounds in the free forms or those of the compounds in the forms of salts also fall within the scope of the present invention.

Among the compounds of the present invention represented by the above formula (I), preferable examples include:

4-[5H-2,3-(2,5-dimethyl-2,5-hexano)-5-methyldibenzo[b,e][1,4]-diazepine-11-yl]benzoic acid (HX600);

4-[5H-2,3-diisopropyl-5-methyldibenzo[b,e][1,4]diazepine-11-yl]benzoic acid (HX610);

4-[5H-2-tert-butyl-5-methyldibenzo[b,e][1,4]diazepine-11-yl]benzoic acid (HX511);

4-[5H-3,4-(1,4-butano)-5-methyldibenzo[b,e][1,4]diazepine-11-yl]benzoic acid (HX545);, 4-[5H-2,3-(2,5-dimethyl-2,5-hexano)-5-methyl-8-nitrodibenzo[b,e]-[1, 4]-diazepine-11-yl]benzoic acid (HX531);

4-[2,3-(2,5-dimethyl-2,5-hexano)dibenzo[b,f][1,4]oxazepine-11-yl]benzoic acid (HX620);

4-[2,3-(2,5-dimethyl-2,5-hexano)dibenzo[b,f][1,4]thiazepine-11-yl]benzoic acid (HX630);

5-[5H-2,3-(2,5-dimethyl-2,5-hexano)-5-methyldibenzo[b,e]
[1,4]-diazepine-11-yl]-2-pyridinecarboxylic acid;
6-[5H-2,3-(2,5-dimethyl-2,5-hexano)-5-methyldibenzo[b,e]
[1,4]-diazepine-11-yl]-3-pyridinecarboxylic acid; and
4-[2,3-(2,5-dimethyl-2,5-hexano)dibenzo[b,e]azepine-11-yl]benzoic acid (HX640), and lower alkyl esters of the above respective compounds, preferably methyl esters (for example, as for HX600, methyl 4-[5H-2,3-(2,5-dimethyl-2,5-hexano)-5-methyldibenzo[b,e][1,4]diazepine-11-yl]benzoate).

Among the compounds of the present invention represented by the formula (II), examples of preferred compounds include, for example, those listed in the table set out below. In these compounds, $R^1$ is a hydrogen atom or methyl group, Y is p-phenylene group, and X is —$NR^7$—. The symbol "Bzl" represents benzyl group, and descriptions such as 7-Me, 8-Et, 8-i-Pro, and 9-t-Bu represent that the compound of formula (II) is substituted with methyl group at the 7-position, ethyl group at the 8-position, isopropyl group at the 8-position, and tert-butyl group at the 9-position, respectively. The descriptions such as 7-$(CH_2)_4$-8 and 7-$C(CH_3)_2CH_2CH_2C(CH_3)_2$-8 represent that the 7-position and the 8-position of the compounds of the formula (II) are bound with —$(CH_2)_4$— and —$C(CH_3)_2 CH_2 CH_2 C(CH_3)_2$—, respectively.

TABLE 1

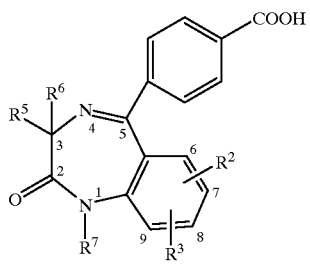

| $R^2$ | $R^3$ | $R^5$ | $R^6$ | $R^7$ |
|---|---|---|---|---|
| H | H | H | H | H |
| 7-Me | H | H | H | H |
| 7-Me | 8-Me | H | H | H |
| 8-Me | 9-Me | H | H | H |
| 7-Et | 8-Et | H | H | H |
| 7-n-Pro | 8-n-Pro | H | H | H |
| 7-i-Pro | 8-i-Pro | H | H | H |
| 7-i-Pro | 8-i-Pro | Me | H | H |
| 7-i-Pro | 8-i-Pro | Et | H | H |
| 7-i-Pro | 8-i-Pro | i-Pro | H | H |
| 7-i-Pro | 8-i-Pro | H | H | Me |
| 7-i-Pro | 8-i-Pro | Me | H | Me |
| 7-i-Pro | 8-i-Pro | Et | H | Me |
| 7-i-pro | 8-i-Pro | Et | Me | Me |
| 7-i-Pro | 8-i-Pro | i-Pro | H | Me |
| 7-i-Pro | 8-i-Pro | i-Pro | H | i-Pro |
| 7-i-Pro | 8-n-Pro | H | H | H |
| 7-t-Bu | 8-t-Bu | Me | H | H |
| 7-t-Bu | 8-t-Bu | Et | H | H |
| 7-t-Bu | 8-t-Bu | i-Pro | H | H |
| 7-t-Bu | 8-t-Bu | H | H | Me |
| 7-t-Bu | 8-t-Bu | H | H | i-Pro |
| 7-t-Bu | 8-t-Bu | Me | H | Me |
| 7-t-Bu | 8-t-Bu | i-Pro | H | Me |
| 7-t-Bu | 8-t-Bu | Et | Me | Me |
| 7-$(CH_2)_4$-8 | H | H | H | H |
| 7-$C(CH_3)_2CH_2CH_2C(CH_3)_2$-8 | H | H | H | H |
| 7-$C(CH_3)_2CH_2CH_2C(CH_3)_2$-8 | Me | H | H | H |
| 7-$C(CH_3)_2CH_2CH_2C(CH_3)_2$-8 | Me | Me | H | H |
| 7-$C(CH_3)_2CH_2CH_2C(CH_3)_2$-8 | Me | Me | Me | H |
| 7-$C(CH_3)_2CH_2CH_2C(CH_3)_2$-8 | Et | H | H | H |
| 7-$C(CH_3)_2CH_2CH_2C(CH_3)_2$-8 | n-Pro | H | H | H |

TABLE 1-continued

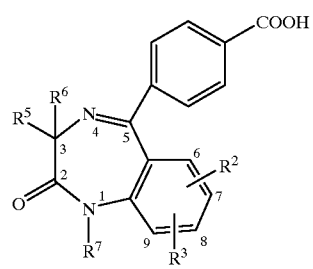

| $R^2$ | $R^3$ | $R^5$ | $R^6$ | $R^7$ |
|---|---|---|---|---|
| 7-$C(CH_3)_2CH_2CH_2C(CH_3)_2$-8 | i-Pro | H | H | H |
| 7-$C(CH_3)_2CH_2CH_2C(CH_3)_2$-8 | H | H | H | Me |
| 7-$C(CH_3)_2CH_2CH_2C(CH_3)_2$-8 | H | H | H | i-Pro |
| 7-$C(CH_3)_2CH_2CH_2C(CH_3)_2$-8 | n-Pro | H | H | Me |
| 7-$C(CH_3)_2CH_2CH_2C(CH_3)_2$-8 | i-Pro | H | H | Me |
| 7-$C(CH_3)_2CH_2CH_2C(CH_3)_2$-8 | i-Pro | H | H | i-Pro |
| 7-$C(CH_3)_2CH_2CH_2C(CH_3)_2$-8 | t-Bu | H | H | H |
| 7-$C(CH_3)_2CH_2CH_2C(CH_3)_2$-8 | t-Bu | H | H | Me |
| 7-$C(CH_3)_2CH_2CH_2C(CH_3)_2$-8 | t-Bu | H | H | i-Pro |
| 7-$C(CH_3)_2CH_2CH_2C(CH_3)_2$-8 | Bzl | H | H | H |
| 7-$C(CH_3)_2CH_2CH_2C(CH_3)_2$-8 | Bzl | H | H | Me |
| 7-$C(CH_3)_2CH_2CH_2C(CH_3)_2$-8 | H | H | H | Bzl |

Among these, examples of particularly preferred compounds include:

4-[1,3-dihydro-7,8-(2,5-dimethyl-2,5-hexano)-2-oxo-2H-1,4-benzodiazepine-5-yl]benzoic acid (HX800);

4-[1,3-dihydro-7,8-(2,5-dimethyl-2,5-hexano)-1-methyl-2-oxo-2H-1,4-benzodiazepine-5-yl]benzoic acid (HX801);

4-[3(S)-methyl-1,3-dihydro-7,8-(2,5-dimethyl-2,5-hexano)-2-oxo-2H-1,4-benzodiazepine-5-yl]benzoic acid (HX810);

4-[1,3-dihydro-7,8-(2,5-dimethyl-2,5-hexano)-1-isopropyl-2-oxo-2H-1,4-benzodiazepine-5-yl]benzoic acid (HX803);

4-[1-benzyl-1,3-dihydro-7,8-(2,5-dimethyl-2,5-hexano)-2-oxo-2H-1,4-benzodiazepine-5-yl]benzoic acid (HX805); and 4-[3(S)-benzyl-1,3-dihydro-7,8-(2,5-dimethyl-2,5-hexano)-2-oxo-2H-1,4-benzodiazepine-5-yl]benzoic acid (HX850), and lower alkyl esters of the above respective compounds, preferably, methyl esters (for example, as for HX800, methyl 4-[1,3-dihydro-7,8-(2,5-dimethyl-2,5-hexano)-2-oxo-2H-1,4-benzodiazepine-5-yl]benzoate).

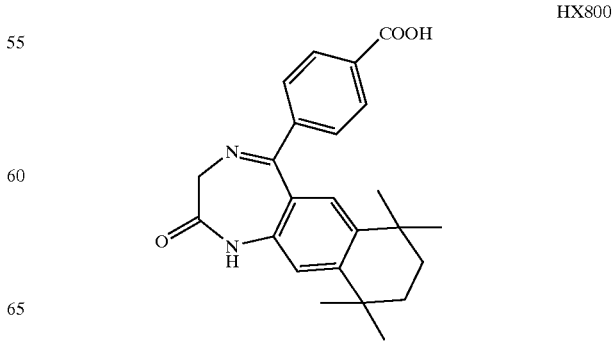

HX800

HX801 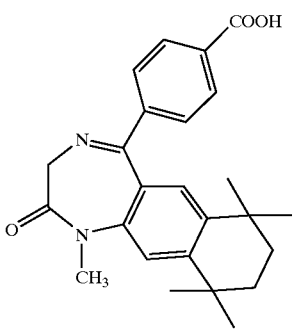

HX810 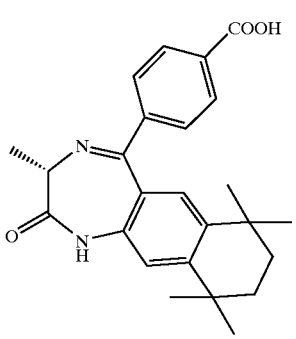

HX803 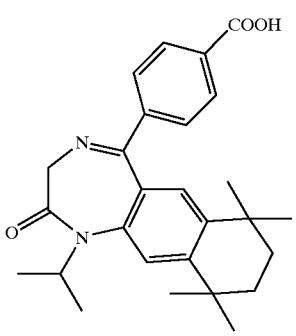

HX805 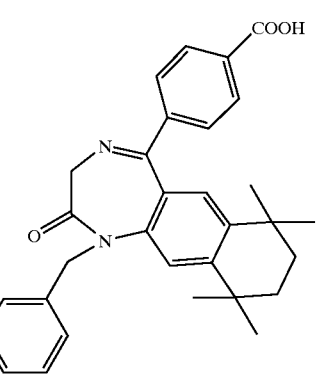

HX850 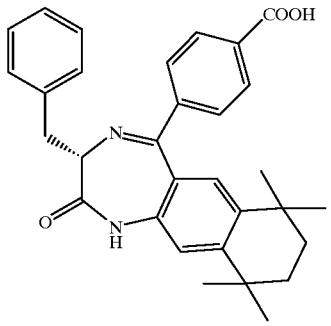

With reference to HX600, HX610, HX511, HX531 and HX545, as being preferred compounds that fall within the formula (I) of the present invention, exemplary preparing methods are shown in the schemes set out below. In addition, as for HX800, HX801 and HX850 being preferred compounds falling within the formula (II) of the present invention, exemplary preparing methods are shown in the same manners in the following schemes. However, the compounds of the present invention and the preparation methods thereof are not limited to those shown in the schemes. The preparation methods of the compounds of the present invention according to the schemes below are further detailed in the examples given in the specification. Therefore, it can be readily understood that any compounds falling within the scope of the present invention can be prepared by appropriately modifying or altering the starting materials, reagents, reaction conditions and the like disclosed in these exemplified methods.

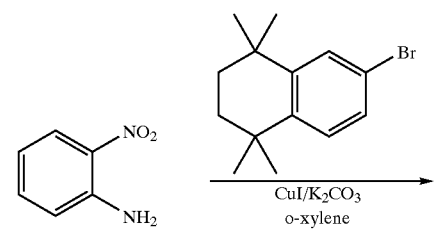

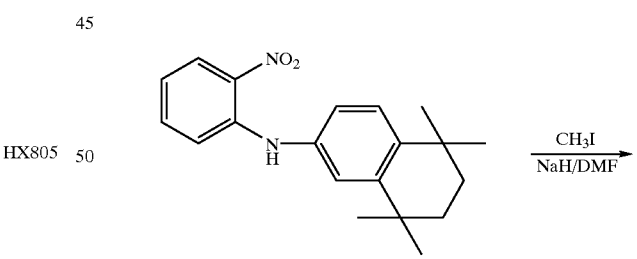

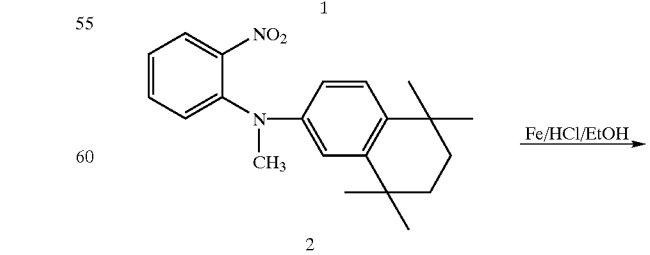

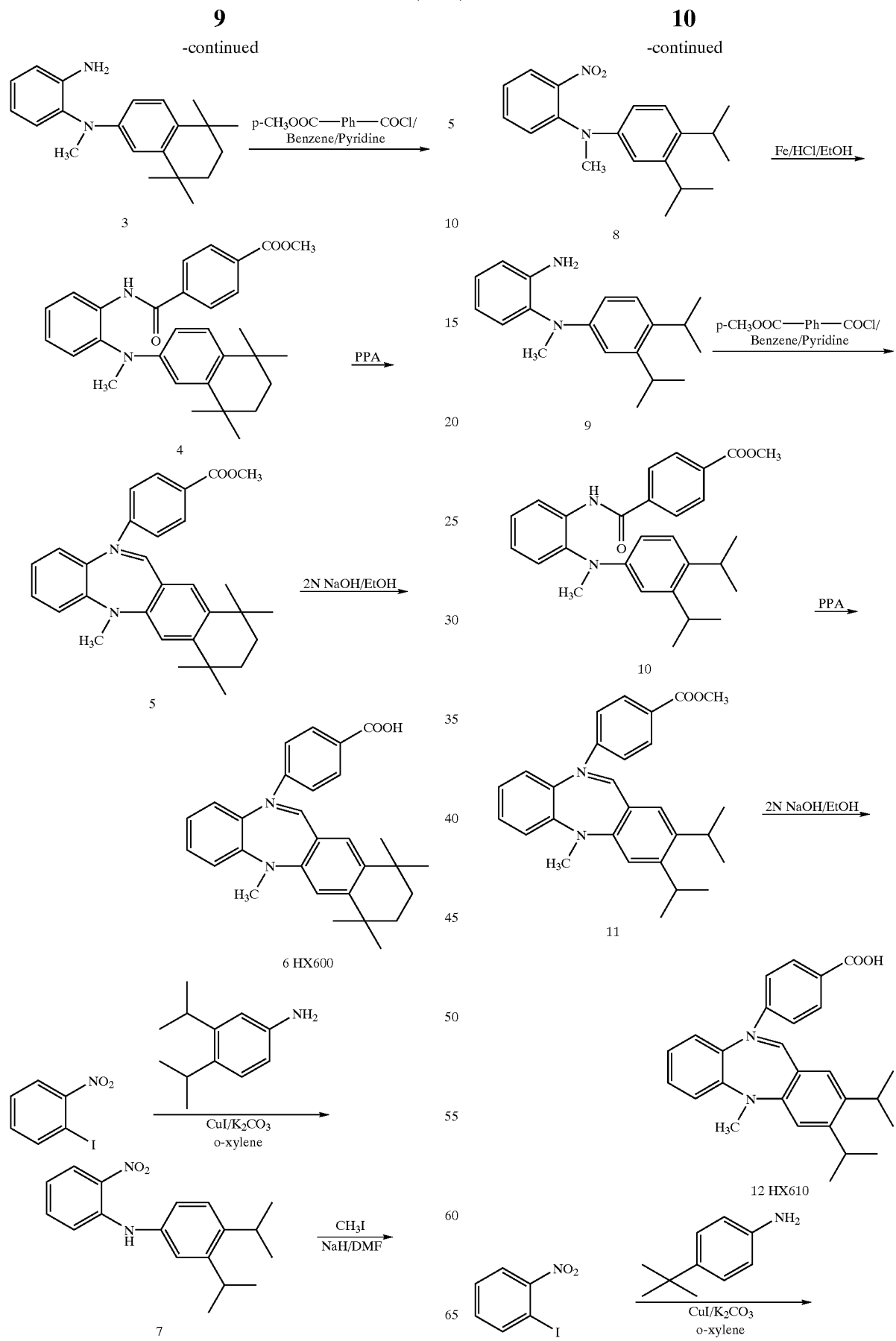

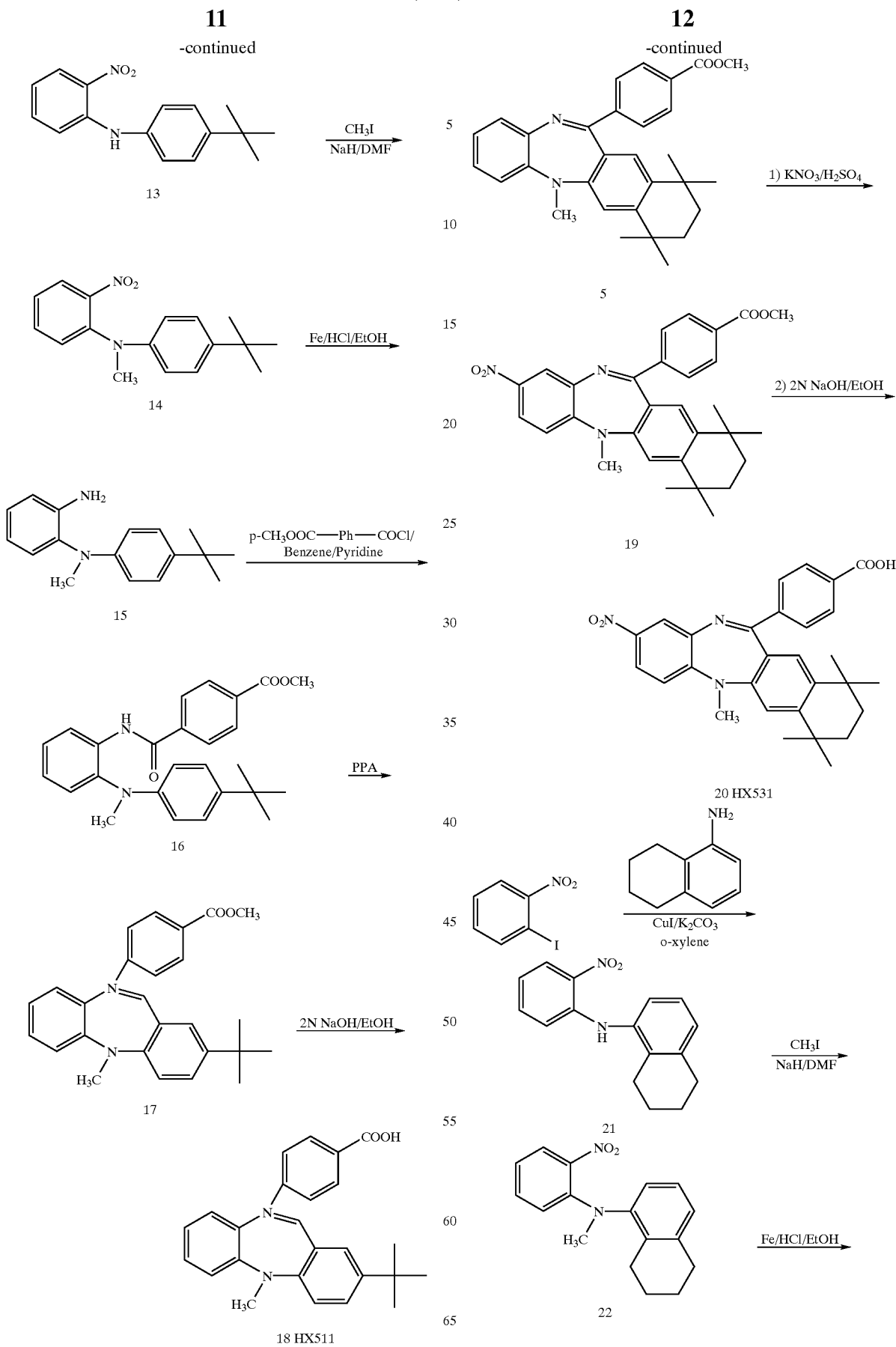

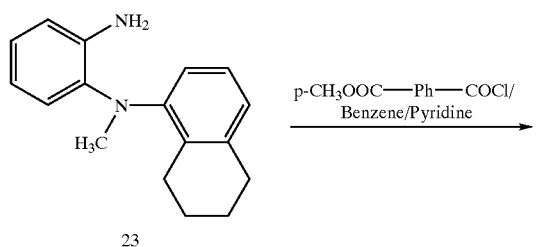
23
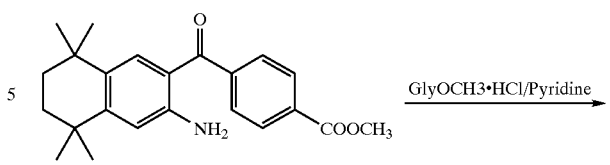
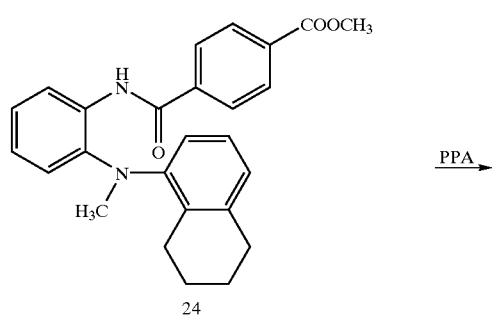
24
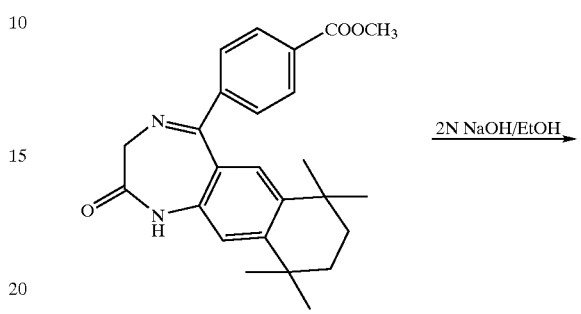
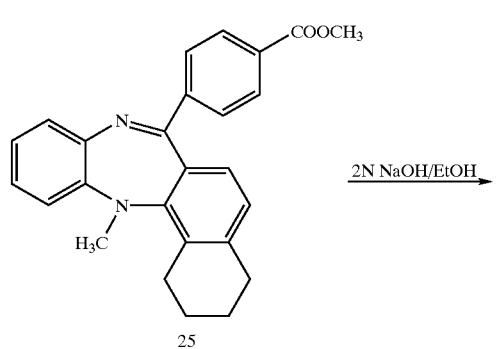
25
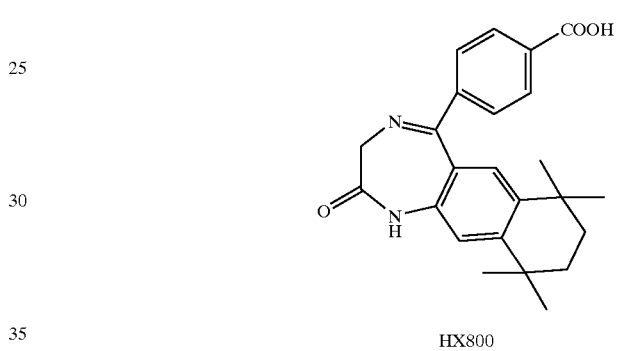
HX800
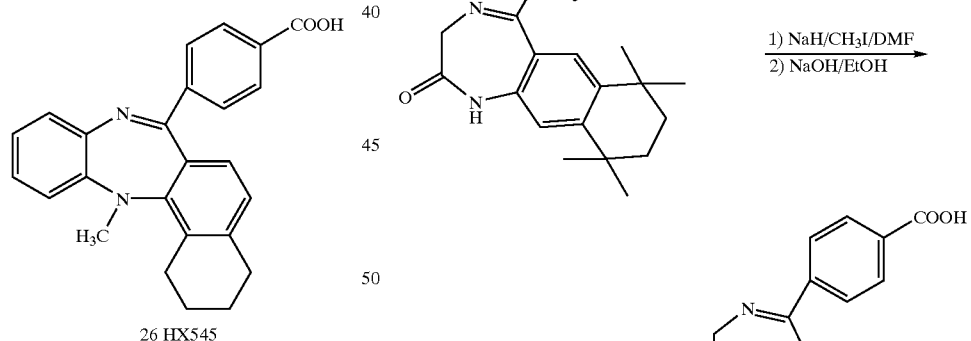
26 HX545
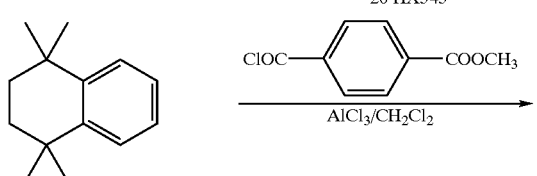
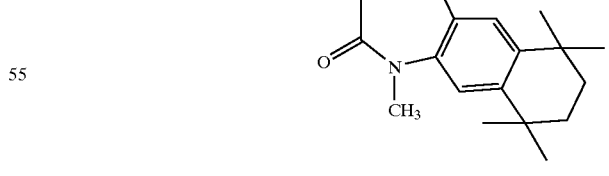
HX801
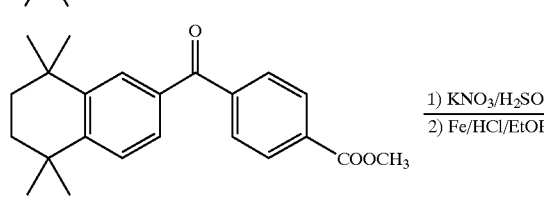
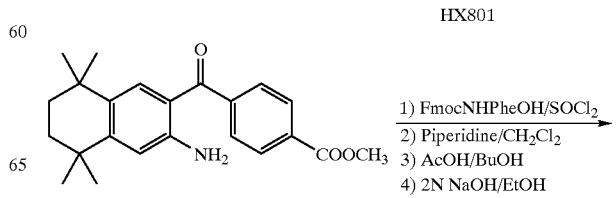

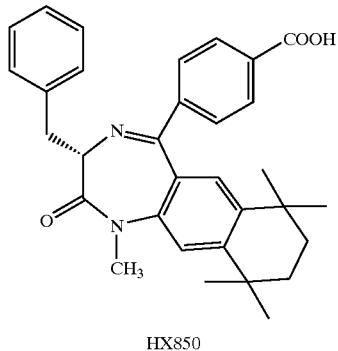

HX850

The compounds of the present invention, per se, have substantially no retinoid-like activity, or they have slight or moderate retinoid-like activities. However, where the compounds of the present invention is subjected to coexistence with a retinoid such as retinoic acid, the physiological activities of the retinoid (typical examples include cell differentiation activity, cell proliferation enhancing activity, life supporting activity and the like) are markedly enhanced.

Although it is not intended to be bound by any specific theory, where a compound of the present invention has retinoid actions, the actions are synergistic. Therefore, where retinoic acid or the aforementioned compounds having the retinoic acid-like biological activities (for example, 4-[(5,6,7,8-tetrahydro-5,5,8,8-tetramethyl-2-naphthalenyl) carbamoyl]benzoic acid: Am80) are administered as medicaments for the preventive or therapeutic treatments of vitamin A deficiency disease, hyperkeratosis of epithelial tissue, psoriasis, allergic diseases, immunological diseases such as rheumatism, bone diseases, leukemia, or cancers, the compounds of the present invention can be used as agents that enhance the activities of the retinoids.

Where the retinoids are not administered for the preventive and therapeutic treatments of the aforementioned diseases, the compounds of the present invention can enhance the activities of retinoic acid inherently existing in living bodies, and thus, the compounds of the present invention, per se, may be administered for the purpose of the preventive and therapeutic treatments of the aforementioned diseases. Furthermore, the compounds of the present invention may be used, in addition to the enhancement of the action of the retinoids, to enhance the activities of physiologically active substances such as, for example, steroid compounds, vitamin D compounds such as vitamin $D_3$, thyroxine and the like that bind to receptors belonging to the intranuclear receptor super family and existing in cell nuclei (Evans, R. M., Science, 240, p.889, 1988).

The medicament comprising the compounds of the present invention may be administered, per se. However, it is preferable that pharmaceutical compositions for oral administrations or parenteral administrations may be administered which can be prepared by methods well known to those skilled in the art. The compounds may be added to medicaments comprising as an active ingredient a retinoid such as retinoic acid, and used as pharmaceutical compositions in the form of so-called combined formulations. Examples of the pharmaceutical compositions suitable for oral administrations include, for example, tablets, capsules, powders, subtilize granules, granules, liquids, syrups and the like. Examples of the pharmaceutical compositions suitable for parenteral administrations include, for example, injections, suppositories, inhalants, eye drops, nasal drops, ointments, creams, patches and the like.

The aforementioned pharmaceutical compositions may be prepared by the addition of pharmacologically and pharmaceutically acceptable additives. Examples of pharmacologically and pharmaceutically acceptable additives include, for example, excipients, disintegrators and disintegrating aids, binders, lubricants, coating agents, colorants, diluents, base materials, dissolving agents and dissolving aids, isotonic agents, pH modifiers, stabilizers, propellants, tackifiers and the like.

The doses of the medicament of the present invention are not particularly limited, and suitable doses can appropriately be chosen for any administration methods whose examples include, for example, where the actions of a retinoid is enhanced by using the medicament of the present invention in combination with the medicament comprising said retinoid such as retinoic acid as an active ingredient, or where the medicament of the present invention is administered to enhance the actions of retinoic acid inherently exist in a living body. For example, for oral administrations, the medicament may be used in a dose of 0.01–1,000 mg per day for adults. Where the medicament of the present invention is used in combination with a medicament comprising a retinoid as an active ingredient, the medicament of the present invention can be administered in any periods of time, i.e., during the period of the retinoid administration or before or after said period.

EXAMPLES

The present invention will be more specifically explained by referring to the following examples. However, the scope of the present invention is not limited to those examples. The compound numbers in the examples correspond to those in the schemes shown above.

Example 1

Preparation of 4-[5H-2,3-(2,5-dimethyl-2,5-hexano)-5-methyldibenzo-[b,e][1,4]diazepine-11-yl]benzoic acid (HX600)

Xylene (40 ml) was added to 6-bromo-1,2,3,4-tetrahydro-1,1,4,4-tetramethylnaphthalene (2.30 g, 8.61 mmol), o-nitroaniline (4.30 g, 31.2 mmol), $K_2CO_3$ (4.30 g, 31.2 mmol), and CuI (347 mg) and the mixture was heated under reflux for 24 hours. The xylene was evaporated under reduced pressure, and the residue was purified by silica gel column chromatography (AcOEt:n-hexane=1:50). The product was recrystallized from hexane to give Compound 1 (2.33 g, 84%).

1H-NMR $CDCl_3$ : 9.49(s, 1H), 8.20(dd, 1H, 8.4 Hz, 1.5 Hz), 7.33(d, 2H, 8.4 Hz), 7.20(dd, 1H, 8.8 Hz, 1.1 Hz), 7.18(d, 1H, 2.2 Hz), 7.04(dd, 1H, 8.4 Hz, 2.2 Hz), 6.73(m, 1H), 1.71(s, 4H), 1.30(s, 6H), 1.28(s, 6H)

NaH (60% in oil, 246 mg, 6.16 mmol, 1.5 eq) was washed with n-hexane and dried. Compound 1 (1.33 g, 4.10 mmol) dissolved in DMF (30 ml) was added to the base and the mixture was stirred at room temperature for 30 minutes. This mixture was added with $CH_3$ I (0.51 ml, 8.20 mmol) and stirred 3 hours. The reaction mixture was poured into ice water and extracted with dichloromethane, and the organic layer was washed with water and saturated brine and dried. The solvent was evaporated under reduced pressure and the residue was purified by silica gel column chromatography (AcOEt:n-hexane=1:40) to give Compound 2 (1.39 g, 100%).

$^1$H-NMR $CDCl_3$ : 7.81(dd, 1H, 8.1 Hz, 1.5 Hz), 7.53(m, 1H), 7.34(dd, 1H, 8.1 Hz, 1.5 Hz), 7.19(m, 1H), 7.14(d, 1H, 8.4 Hz), 6.67(d, 1H, 2.6 Hz), 6.61(dd, 1H, 8.4 Hz, 2.6 Hz), 3.29(s, 3H), 1.63(s, 4H), 1.23(s, 6H), 1.18(s, 6H)

Compound 2 (1.41 g, 4.17 mmol) was suspended in water (20 ml) and ethanol (40 ml), and added with concentrated hydrochloric acid (6.0 ml). The mixture was added with iron powder (2.2 g) and heated under reflux for 30 minutes. The reaction mixture was filtered to remove solid iron powder and the filtrate was extracted with ethyl acetate. The organic layer was washed with water and saturated brine and then dried. The solvent was evaporated under reduced pressure to give Compound 3 (1.25 g, 99%).

$^1$H-NMR CDCl$_3$ : 7.11(d, 1H, 8.8 Hz), 7.06(m, 2H), 6.81 (dd, 1H, 8.1 Hz, 1.5 Hz), 6.75(m, 1H), 6.61(d, 1H, 2.6 Hz), 6.44(dd, 1H, 8.4 Hz, 2.6 Hz), 3.82(brs, 2H), 3.18(s, 3H), 1.65(s, 4H), 1.23(s, 6H), 1.23(s, 6H)

Compound 3 (1.25 g, 4.06 mmol) was dissolved in dried benzene (25 ml), and added with pyridine (0.5 ml). The mixture was added with terephthalic acid monomethyl ester chloride (966 mg, 4.87 mmol) and stirred at room temperature for 18 hours. The reaction mixture was added with ice water and diluted hydrochloric acid and then extracted with ethyl acetate. The organic layer was dried, and the solvent was evaporated under reduced pressure to give a crude product (2.10 g). The product was purified by silica gel column chromatography (AcOEt:n-hexane=1:20) to give Compound 4 (1.72 g, 90%).

$^1$H-NMR CDCl$_3$ : 8.57(dd, 1H, 8.1 Hz, 1.5 Hz), 8.45(s, 1H), 7.99(d, 2H, 8.8 Hz), 7.45(d, 2H, 8.8 Hz), 7.32(m, 1H), 7.18–7.26(m, 2H), 6.68(d, 1H, 2.6 Hz), 6.60(dd, 1H, 8.4 Hz, 2.6 Hz), 3.93(s, 3H), 3.31(s, 3H), 1.64(s, 4H), 1.24(s, 6H), 1.16(s, 6H)

Compound 4 (1.72 g, 3.65 mmol) was added with polyphosphoric acid (15.8 g) and stirred at 110° C. for 2 hours and 40 minutes. The reaction mixture was added with water and then extracted with dichloromethane, and the organic layer was washed with saturated brine. The solvent was evaporated under reduced pressure and the resulting residue was dried, the residue was purified by silica gel column chromatography (AcOEt:n-hexane=1:30) to give the compound of the present invention (Compound 5: methyl 4-[5H-5-methyl-7,8-(2,5-dimethyl-2,5-hexano)dibenzo[b,e]diazepine-10-yl]benzoate (1.41 g, 86%). m.p..238° C.

$^1$H-NMR CDCl$_3$ : 8.07(d, 2H, 8.8 Hz), 7.88(d, 2H, 8.4 Hz), 7.31(dd, 1H, 7.7 Hz, 1.8 Hz), 7.15(m, 1H), 7.09(m, 1H), 6.98(dd, 1H, 6.6 Hz, 1.8 Hz), 6.92(s, 1H), 6.87(s, 1H), 3.95(s, 3H), 3.26(s, 3H), 1.63(m, 4H), 1.32(s, 3H), 1.26(s, 3H), 1.12(s, 3H), 1.04(s, 3H)

Anal. Calc. for $C_{30}H_{32}N_2O_2$ C:79.61, H:7.13, N:6.19; Found C:79.56, H:7.27, N:6.12

Compound 5 (43 mg, 0.095 mmol) was suspended in ethanol (4 ml) and 2N NaOH (1.5 ml) and the suspension was stirred at room temperature for 1 hour and 10 minutes. The reaction mixture was adjusted to pH 2 using 2N HCl and then extracted with dichloromethane. The organic layer was washed with water and saturated brine and dried, the solvent was then evaporated under reduced pressure. The resulting residue was dried to give compound of the present invention: HX600 (Compound 6, 37.1 mg, 89%). m.p.282° C.

$^1$H-NMR CDCl$_3$ : 8.15(d, 2H, 8.4 Hz), 7.91(d, 2H, 8.4 Hz), 7.33(dd, 1H, 7.7 Hz, 1.5 Hz), 7.15(m, 1H), 7.09(m, 1H), 6.98(dd, 1H, 7.7 Hz, 1.1 Hz), 6.93(s, 1H), 6.88(s, 1H), 3.27(s, 3H), 1.62(m, 4H), 1.32(s, 3H), 1.27(s, 3H), 1.13(s, 3H), 1.05(s, 3H)

MS M$^+$438

Anal. Calc. for or $C_{29}H_{30}N_2O_2$ C:79.42, H:6.89, N:6.39; Found C:79.12, H:7.15, N:6.25

Example 2
Preparation of 4-[5H-2,3-diisopropyl-5-methyldibenzo[b,e][1,4]diazepine-11-yl]benzoic acid (HX610)

3,4-Diisopropylaniline (107 mg, 0.60 mmol), o-iodonitrobenzene (180 mg, 0.72 mmol), K$_2$CO$_3$ (83 mg, 0.60 mmol), and CuI (34 mg) were added to xylene (5 ml) and the mixture was heated under reflux for 18 hours. The xylene was evaporated under reduced pressure, and the residue was purified by silica gel column chromatography (AcOEt:n-hexane=1:50) to give Compound 7 (59 mg, 33%).

$^1$H-NMR CDCl$_3$ : 9.50(s, 1H), 8.20(dd, 1H, 8.4 Hz, 1.5 Hz), 7.40(m, 1H), 7.29(d, 1H, 8.1 Hz), 7.20(dd, 1H, 8.8 Hz, 1.1 Hz), 7.13(d, 1H, 2.2 Hz), 7.08(dd, 1H, 8.4 Hz, 2.2 Hz), 6.73(m, 1H), 3.27(m, 2H),1.25(m, 12H)

NaH (60% in oil, 16 mg, 0.40 mmol, 2 eq) was washed with n-hexane and dried. Compound 7 (58 mg, 0.20 mmol) dissolved in DMF (5 ml) was added to the base and the mixture was stirred at room temperature for 30 minutes. The mixture was added with CH$_3$I (0.04 ml, 0.60 mmol) and then stirred for 3 hours. The reaction mixture was poured into ice water and extracted with dichloromethane. The organic layer was washed with water and saturated brine. After dryness, the solvent was evaporated under reduced pressure to give Compound 8 (57 mg, 93%).

$^1$H-NMR CDCl$_3$ : 7.81(dd, 1H, 8.1 Hz, 1.5 Hz), 7.53(m, 1H), 7.34(dd, 1H, 8.1 Hz, 1.5 Hz), 7.18(m, 1H), 7.10(d, 1H, 9.2 Hz), 6.62(m, 2H), 3.31(s, 3H), 3.17(septet, 2H), 1.19(d, 6H, 7.0 Hz), 1.14(d, 6H, 7.0 Hz)

Compound 8 (52.5 mg, 0.17 mmol) was suspended in water (2 ml) and ethanol (4 ml), and added with concentrated hydrochloric acid (0.5 ml). The mixture was added with iron powder (200 mg) and heated under reflux for 30 minutes. The reaction mixture was filtered to remove solid iron powder, and the filtrate was extracted with ethyl acetate. The organic layer was washed with water and saturated brine and dried, the solvent was then evaporated under reduced pressure to give Compound 9 (40.0 mg, 84%).

$^1$H-NMR CDCl$_3$ : 7.07(m, 3H), 6.82(dd, 1H, 7.7 Hz, 1.5 Hz), 6.76(m, 1H), 6.59(d, 1H, 2.9 Hz), 6.46(dd, 1H, 8.4 Hz, 2.6 Hz), 3.84(brs, 2H), 3.20(s, 3H), 3.18(m, 2H), 1.19(m, 12H)

Compound 9 (39 mg, 0.14 mmol) was dissolved in dry benzene (5 ml) and added with pyridine (0.1 ml). The mixture was added with terephthalic acid monomethyl ester chloride (36 mg, 0.18 mmol) and stirred at room temperature for 3 hours. The reaction mixture was added with ice water and diluted hydrochloric acid and then extracted with ethyl acetate. The organic layer was dried and the solvent was evaporated to give a crude product (67.3 mg). The product was purified by silica gel column chromatography (AcOEt:n-hexane=1:20) to give Compound 10 (44.4 mg, 71%).

$^1$H-NMR CDCl$_3$ : 8.58(d, 1H, 9.5 Hz), 8.47(m, 1H), 7.98(d, 2H, 8.4 Hz), 7.46(d, 2H, 8.4 Hz), 7.32(m, 1H), 7.22(m, 2H), 7.15(d, 1H, 8.4 Hz), 6.66(d, 1H, 2.9 Hz), 6.60(dd, 1H, 8.4 Hz 2.6 Hz), 3.93(s, 3H), 3.31(s, 3H), 3.21(septet, 2H), 1.20(d, 6H, 6.6 Hz), 1.13(d, 6H, 7.0 Hz)

Compound 10 (44 mg, 0.10 mmol) was added with polyphosphoric acid (1.2 g) and stirred at 120° C. for 1 hour. The reaction mixture was added with water and extracted with dichloromethane. The organic layer was washed with saturated brine and dried, and the solvent was then evaporated under reduced pressure. The resulting residue was dried and then purified by silica gel column chromatography (AcOEt:n-hexane=1:30) to give the compound of the present invention (Compound 11: methyl 4-[5H-5-methyl-7,8-diisopropyldibenzo[b,e]diazepine-10-yl]benzoate) (19.2 mg, 45%).

$^1$H-NMR CDCl$_3$ : 8.07(d, 2H, 8.8 Hz), 7.87(d, 2H, 8.4 Hz), 7.31(dd, 1H, 7.7 Hz, 1.8 Hz), 7.15(m, 1H), 7.08(m, 1H), 6.98(m, 1H), 6.99(s, 1H), 6.97(s, 1H), 3.95(s, 3H), 3.27(s, 3H), 3.23(m, 1H), 3.13(m, 1H), 1.28(d, 3H, 6.6 Hz), 1.26(d, 3H, 7.0 Hz), 1.08(d, 3H, 7.0 Hz), 1.01(d, 3H, 7.0 Hz)

Compound 11 (18 mg, 0.043 mmol) was suspended in ethanol (2 ml) and 2N NaOH (1 ml) and stirred at room temperature for 40 minutes. The reaction mixture was adjusted to pH 2 using 2N HCl and extracted with dichloromethane. The organic layer was washed with water and saturated brine, and the solvent was then evaporated under reduced pressure. The resulting residue was dried to give the compound of the present invention: HX610 (Compound 12, 15.6 mg, 88%). The product was recrystallized from a mixture of ethanol/water to give 10.5 mg of purified compound. m.p.263° C.
$^1$H-NMR $CDCl_3$ : 8.14(d, 2H, 8.8 Hz), 7.91(d, 2H, 8.4 Hz), 7.32(dd, 1H, 7.7 Hz, 1.8 Hz), 7.16(m, 1H), 7.10(m, 1H), 6.99(dd, 1H, 8.1 Hz, 1.1 Hz), 6.90(s, 1H), 6.83(s, 1H), 3.28(s, 3H), 3.24(m, 1H), 3,14(m, 1H), 1.28(d, 3H, 7.0 Hz), 1.23(d, 3H, 6.6 Hz), 1.10(d, 3H, 7.0 Hz), 1.02(d, 3H, 7.0 Hz)
Anal. Calc. for $C_{27}H_{28}N_2O_2$ C:78.61, H:6.84, N:6.79; Found C:78.36, H:6.92, N:6.67

Example 3
Preparation of 4-[5H-2-tert-butyl-5-methyldibenzo[b,e][1,4] diazepine-11-yl]benzoic acid (HX511)

4-tert-Butylaniline (761 mg, 5.1 mmol), $K_2CO_3$ (697, 5.1 mmol), CuI 95 mg, and o-xylene (10 ml) were added to o-iodonitrobenzene (1.25 g, 5.0 mmol) and the mixture was stirred at 150° C. for 11 hours. The reaction mixture was purified by silica gel column chromatography (AcOEt:n-hexane=1:40) to give Compound 13 (529.1 mg, 39%).
$^1$H-NMR $CDCl_3$ : 9.48(s, 1H), 8.20(dd, 1H, 8.4 Hz, 1.5 Hz), 7.43(d, 2H, 8.8 Hz), 7.35(m, 1H), 7.22(m, 3H), 6.76(m, 1H), 1.35(s, 9H)

NaH (60% in oil, 73 mg, 1.82 mmol) was washed with hexane and dried. DMF (1 ml) was added to the base and the resulting suspension was added with Compound 13 (241.7 mg, 0.895 mmol) dissolved in DMF (5 ml). The reaction mixture was stirred at room temperature for 20 minutes, added with methyl iodide (0.18 ml, 2.78 mmol, 3 eq) and stirred for 3 hours. The reaction mixture was poured into ice water and extracted with dichloromethane. The organic layer was washed with water and saturated brine and dried, and then concentrated under reduced pressure to give Compound 14 (245.3 mg, 97%).
$^1$H-NMR $CDCl_3$ : 7.83(dd, 1H, 8.1 Hz, 1.5 Hz), 7.57(m, 1H), 7.36(dd, 1H, 8.1 Hz, 1.5 Hz), 7.22(d, 2H, 8.8 Hz), 6.70(d, 2H, 9.2 Hz), 3.29(s, 3H), 1.27(s, 9H)

Water (4 ml), ethanol (8 ml), iron powder (406 mg), and concentrated hydrochloric acid (1.0 ml) were added to Compound 14 (240 mg, 0.845 mmol) and the mixture was heated under reflux for 20 minutes. The reaction mixture was added with ethyl acetate and filtered. The filtrate was washed with water and saturated brine. The organic layer was dried and concentrated under reduced pressure to give Compound 15 (184.6 mg, 86%).
$^1$H-NMR $CDCl_3$ : 7.22(d, 2H, 8.8 Hz), 7.08(m, 1H), 7.04 (dd, 1H, 8.1 Hz, 1.5 Hz), 6.82(dd, 1H, 7.7 Hz, 1.5 Hz), 6.77(m, 1H), 6.61(d, 2H, 8.8 Hz), 3.83 (brs, 2H), 3.20(s, 3H), 1.28(s, 9H)

Compound 15 (174 mg, 0.685 mmol) was dissolved in dry benzene (7 ml) and added with pyridine (0.1 ml, 1.25 mmol). The mixture was added with terephthalic acid monomethyl ester chloride (163 mg, 0.823 mmol) and stirred at room temperature for 2 hours and 15 minutes. The reaction mixture was added with ice water and diluted hydrochloric acid and then extracted with ethyl acetate. The organic layer was dried and the solvent was evaporated under reduced pressure to give a crude product (320.1 mg). This product was purified by silica gel column chromatography (AcOEt:n-hexane=1:20) to give Compound 16 (206.7 mg, 73%).
$^1$H-NMR $CDCl_3$ : 8.60(d, 1H, 7.0 Hz), 8.57(s, 1H), 8.00(d, 2H, 8.4 Hz), 7.53(d, 2H, 8.4 Hz), 7.33(m, 1H), 7.28(d, 2H, 8.8 Hz), 7.21(m, 2H), 6.72(d, 2H, 8.8 Hz), 3.93(s, 3H), 3.28(s, 3H), 1.29(s, 9H)

Compound 16 (202.6 mg, 0.487 mmol) was added with polyphosphoric acid (2.5 g) and the mixture was stirred at 130° C. for 2 hours. Additional polyphosphoric acid (2.0 g) was added and stirring was continued for 1 hour. The reaction mixture was added with water and extracted with dichloromethane. The organic layer was concentrated and dried to give a crude product (164.9 mg). This crude product was purified by silica gel column chromatography (AcOEt:n-hexane=1:40 → 1:20), and the resulting purified product was further purified by silica gel column chromatography (AcOEt:n-hexane=1:20) to give Compound 17 (22.0 mg, 11%).
$^1$H-NMR $CDCl_3$ : 8.08(d, 2H, 8.4 Hz), 7.86(d, 2H, 8.4 Hz), 7.42(dd, 1H, 8.4 Hz, 2.2 Hz), 7.32(dd, 1H, 7.7 Hz, 1.8 Hz), 7.15(m, 1H), 7.09(m, 1H), 6.98(m, 3H), 3.95(s, 3H), 3.26(s, 3H), 1.18(s, 9H)

Compound 17 (20.1 mg, 0.05 mmol) was added with 2N NaOH (1.0 ml) and ethanol (2.0 ml) and the mixture was stirred for 3 hours and 15 minutes. The reaction mixture was acidified by adding 2N hydrochloric acid and extracted with dichloromethane. The organic layer was washed with water and saturated brine and dried, and the solvent was then concentrated under reduced pressure. The resulting crude product was purified by silica gel column chromatography (dichloromethane:methanol=20:1) to give the compound of the present invention: HX511 (Compound 18, 16.5 mg, 85%). The product was recrystallized from a mixture of ethanol/water to give purified compound. m.p.249° C.
$^1$H-NMR $CDCl_3$ : 8.14(d, 2H, 8.4 Hz), 7.90(d, 2H, 8.4 Hz), 7.43(dd, 1H, 8.4 Hz, 2.2 Hz), 7.32(dd, 1H, 7.7 Hz, 1.8 Hz), 7.15(m, 1H), 7.09(m, 1H), 6.98(m, 3H), 3.26(s, 3H), 1.19(s, 9H)
Anal. Calc. for $C_{25}H_{24}N_2O_2$ C:78.10, H:6.29, N:7.29; Found C:77.92, H:6.40, N:7.13

Example 4
Preparation of 4-[5H-2,3-(2,5-dimethyl-2,5-hexano)-5-methyl-8-nitrodibenzo[b,e][1,4]diazepine-11-yl]benzoic acid (HX531)

Compound 5 (methyl ester of HX600, 102 mg, 0.226 mmol) was dissolved in concentrated sulfuric acid (5 ml) and the solution was added with $KNO_3$ (36.5 mg, 0.36 mmol) under ice cooling. After 1 hour, the reaction mixture was poured into ice water and extracted with dichloromethane. The organic layer was washed with saturated aqueous sodium hydrogen carbonate, water, and brine successively and dried, and the solvent was then evaporated under reduced pressure to give a crude product (102 mg). This crude product was purified by silica gel column chromatography (AcOEt:n-hexane=1:20) to give Compound 19 (19.3 mg, 17%).
$^1$H-NMR $CDCl_3$ : 8.14(d, 1H, 2.6 Hz), 8.11(d, 2H, 8.8 Hz), 8.01(dd, 1H, 8.8 Hz, 2.6 Hz), 7.89(d, 1H, 8.8 Hz), 6.93(s, 1H), 6.91(s,1H), 3.97(s,3H), 3.32(s, 3H), 1.66(m, 4H), 1.32 (s, 3H), 1.28(s, 3H), 1.14(s, 3H), 1.07(s, 3H)

Compound 19 (17.3 mg, 0.035 mmol) was added with 2N NaOH (1.0 ml) and ethanol (2.0 ml) and the mixture was stirred at room temperature for 90 minutes. The reaction mixture was acidified using 2N HCl. and extracted with dichloromethane. The organic layer was washed with water and saturated brine and dried, and the solvent was then evaporated under reduced pressure to give the compound of the present invention: HX531 (Compound 20, 15.0 mg, 89%). The product was recrystallized from a mixture of ethanol/water to give purified compound. m.p.>300° C.
$^1$H-NMR CDCl$_3$ : 8.15(m, 3H), 8.01(dd, 1H, 8.8 Hz, 2.6 Hz), 7.90(d, 2H, 7.3 Hz), 7.00(d, 1H, 9.2 Hz), 6.93(s, 1H), 6.92(s, 1H), 3.31(s, 3H), 1.65(m, 4H), 1.32(s, 3H), 1.27(s, 3H), 1.14(s, 3H), 1.07(s, 3H)
Anal. Calc. for C$_{29}$H$_{29}$N$_3$O$_4$ C:72.03, H:6.04, N:8.69; Found C:71.89, H:6.25, N:8.54

Example 5

Preparation of 4-[5H-3,4-(1,4-butano)-5-methyldibenzo[b,e][1,4]diazepine-11-yl]benzoic acid (HX545)

Xylene (40 ml) was added to 5,6,7,8- tetrahydro-1-naphthylamine (1.83 g, 12.43 mmol), o-iodonitrobenzene (3.1 g, 12.43 mmol), K$_2$CO$_3$ (1.72 g, 12.43 mmol), and CuI (217 mg), and the mixture was heated under reflux for 18 hours. Then, the xylene was evaporated under reduced pressure and the resulting residue was purified by silica gel column chromatography (AcOEt:n-hexane=1:50) to give Compound 21. (736 mg, 22%).
$^1$H-NMR CDCl$_3$ : 9.30(s, 1H), 8.20(dd, 1H, 8.8 Hz, 1.5 Hz), 7.32(m, 1H), 7.15(m, 2H), 7.04(d, 1H, 7.3 Hz), 6.90(dd, 1H, 8.4 Hz, 1.1 Hz), 6.72(m, 1H), 2.83(m, 2H), 2.64(m, 2H), 1.79(m, 4H)

NaH (60% in oil, 114 mg, 2.84 mmol, 2 eq) was washed with hexane and dried. Compound 21 (381 mg, 1.42 mmol) dissolved in DMF (8 ml) was added to the base and the mixture was stirred at room temperature for 15 minutes. This mixture was added with methyl iodide (0.37 ml, 5.68 mmol) and stirred for 3 hours and 30 minutes. The reaction mixture was poured into ice water and extracted with dichloromethane. The organic layer was dried, and the solvent was then evaporated under reduced pressure to give a crude product. This crude product was purified by silica gel column chromatography (AcOEt:n-hexane=1:100) and the resulting compound was washed with water and saturated brine. After dryness, the solvent was evaporated to give Compound 22 (293 mg, 73%).
$^1$-NMR CDCl$_3$ : 7.67(dd, 1H, 8.1 Hz, 1.8 Hz), 7.34(m, 1H), 7.08(t, 1H, 7.7 Hz), 6.97(d, 1H, 7.3 Hz), 6.86(m, 3H), 3.16(s, 3H), 2.81(m, 2H), 2.57(m, 2H), 1.76(m, 4H)

Compound 22 (101.6 mg, 0.36 mmol) was suspended in a mixture of water (2 ml) and ethanol (6 ml) and added with concentrated hydrochloric acid (0.5 ml). The mixture was added with iron powder (201 mg) and heated under reflux for 10 minutes. The reaction mixture was filtered to remove solid materials, and the filtrate was extracted with ethyl acetate. The organic layer was washed with water and saturated brine and dried, and then the solvent was evaporated under reduced pressure to give Compound 23 (81.1 mg, 89%).
$^1$H-NMR CDCl$_3$ : 7.13(t, 1H, 7.7 Hz), 7.03(d, 1H, 7.3 Hz), 6.93(m, 1H), 6.83(d, 1H, 7.0 Hz), 6.75(dd, 1H, 7.7 Hz, 1.1 Hz), 6.64(m, 2H), 3.96(brs, 2H), 3.05(s, 3H), 2.76(m, 2H), 2.15(m, 2H), 1.65(m, 4H)

Compound 23 (81 mg, 0.32 mmol) was dissolved in dry benzene (5 ml), and the solution was added with pyridine (0.1 ml). The solution was added with terephthalic acid monomethyl ester chloride (79.6 mg, 0.40 mmol) and stirred at room temperature for 16 hours. The reaction mixture was added with ice water and diluted hydrochloric acid and then extracted with ethyl acetate. The organic layer was dried and the solvent was evaporated under reduced pressure. The resulting residue was purified by silica gel column chromatography (AcOEt:n-hexane=1:20 → 1:10) to give Compound 24 (113.9 mg, 86%)

$^1$H-NMR CDCl$_3$ : 8.45(s, 1H), 8.36(d, 1H, 7.7 Hz), 8.09(d, 2H, 8.1 Hz), 7.68(d, 2H, 8.4 Hz), 7.13(m, 3H), 6.99(dd, 1H, 8.1 Hz, 1.5 Hz), 6.96(d, 1H, 7.3 Hz), 6.91(d, 1H, 7.7 Hz), 3.96(s, 3H), 3.10(s, 3H), 2.73(m, 2H), 2.31(m, 2H), 1.60(m, 2H), 1.51(m, 2H)

Polyphosphoric acid (1.83 g) was added to Compound 24 (113 mg, 0.273 mmol) and the mixture was stirred at 130° C. for 1 hour. The reaction mixture was added with water and then extracted with dichloromethane, and the organic layer was washed with saturated brine. After dryness, the solvent was evaporated under reduced pressure and the resulting residue was purified by silica gel column chromatography (AcOEt:n-hexane=1:40 → 1:20) to give Compound 25 (67.9 mg, 63%).
$^1$H-NMR CDCl$_3$ : 8.10(d, 2H, 8.8 Hz), 7.91(d, 2H, 8.4 Hz), 7.40(dd, 1H, 8.1 Hz, 2.2 Hz), 7.25(m, 1H), 7.20(m, 2H), 6.89(d, 1H, 8.1 Hz), 6.82(d, 1H, 8.1 Hz), 3.95(s, 3H), 3.06(s, 3H), 3.02(m, 2H), 2.78(m, 2H), 1.95(m, 1H), 1.85(m, 1H), 1.75(m, 2H)

2N NaOH (2.0 ml) and ethanol (5.0 ml) were added to Compound 25 (66.3 mg, 0.167 mmol), and the mixture was stirred at room temperature for 1 hour and 15 minutes. The reaction mixture was acidified using 2N HCl and extracted with dichloromethane. The organic layer was washed with water and saturated brine and dried, and the solvent was then evaporated under reduced pressure to give the compound of the present invention: HX545 (Compound 26, 60.7 mg, 95%). The product was recrystallized from a mixture of ethanol/water to give purified compound. m.p.273° C.
$^1$H-NMR CDCl$_3$ : 8.17(d, 2H, 8.8 Hz), 7.95(d, 2H, 8.4 Hz), 7.42(dd, 1H, 7.7 Hz, 1.8 Hz), 7.22(m, 3H), 6.91(d, 1H, 8.1 Hz), 6.83(d, 1H, 8.1 Hz), 3.07(s, 3H), 3.02(m, 2H), 2.80(m, 2H), 1.95(m, 2H), 1.84(m, 2H), 1.75(m, 4H)
Anal. Calc. for C$_{25}$H$_{22}$N$_2$O$_2$ C:78.51, H:5.80, N:7.32; Found C:78.32, H:5.83, N:7.13

Example 6

Preparation of 4-[2,3-(2,5-dimethyl-2,5-hexano)-dibenzo[b,f][1,4]oxazepine-11-yl]benzoic acid (HX620)

DMSO (5 ml) was added to 5,6,7,8-tetrahydro-5,5,8,8-tetramethyl-2-naphthol (97 mg, 0.475 mmol), o-chloronitrobenzene (77 mg, 0.48 mmol) and potassium hydroxide (27 mg, 0.48 mmol), and the mixture was stirred at 90° C. for 17 hours and 30 minutes. To the reaction mixture, water, dichloromethane, and concentrated hydrochloric acid (1 ml) were added, and the organic layer was washed with diluted hydrochloric acid and brine. After dryness, the solvent was evaporated under reduced pressure to give a crude product (139.7 mg). This crude product was purified by silica gel column chromatography (AcOEt:n-hexane=1:30) to give o-(5,6,7,8-tetrahydro-5,5,8,8-tetramethyl-2-naphtalenyl)-2-nitrophenol (Compound 27, 103.1 mg, 67%, colorless oil)
$^1$H-NMR CDCl$_3$ : 7.93(dd, 1H, 8.1 Hz, 1.5 Hz), 7.46(m, 1H), 7.29(d, 1H, 8.8 Hz), 7.14(m, 1H), 7.01(d, 1H, 2.6 Hz), 6.99(dd, 1H, 8.4 Hz, 1.1 Hz), 6.80(dd, 1H, 8.4 Hz, 2.6 Hz), 1.69(s, 4H), 1.28(s, 6H), 1.25(s, 6H)

Compound 27 was suspended in water (2 ml) and ethanol (6 ml), and the suspension was added with concentrated hydrochloric acid (0.5 ml). The mixture was added with iron powder (220 mg) and then heated under reflux for 30 minutes. The reaction mixture was filtered to remove solid materials and the filtrate was extracted with ethyl acetate. The organic layer was washed with water and saturated brine and dried, and the solvent was then evaporated under reduced pressure to give o-(5,6,7,8-tetrahydro-5,5,8,8-tetramethyl-2-naphtalenyl)-2-aminophenol (Compound 28, 80.5 mg, 85%).

$^1$H-NMR CDCl$_3$ : 7.21(d, 1H, 8.8 Hz), 6.97(d, 1H, 2.9 Hz), 6.95(m, 1H), 6.85(dd, 1H, 8.1 Hz, 1.5 Hz), 6.82(dd, 1H, 7.7 Hz, 1.5 Hz), 6.70(m, 2H), 3.82(brs, 2H), 1.68(s, 4H), 1.26(s, 6H), 1.25(s, 6H)

Compound 28 (80.5 mg, 0.264 mmol) was dissolved in dry benzene (5 ml) and added with pyridine (0.1 ml, 1.25 mmol). Terephthalic acid monomethyl ester chloride (63 mg, 0.317 mmol) was added to this solution, and the solution was stirred at room temperature for 16 hours and 30 minutes. The reaction mixture was added with ice water and diluted hydrochloric acid, and extracted with ethyl acetate. After dryness, the solvent was evaporated under reduced pressure to give a crude product (133 mg). This crude product was purified by silica gel column chromatography (AcOEt:n-hexane=1:20 → 1:2) to give methyl 4-[2-(o-(5,6,7,8-tetrahydro-5,5,8,8-tetramethylnaphtalenyl)aminocarbamoyl]benzoate (Compound 29, 115.8 mg, 94%).

$^1$H-NMR CDCl$_3$ : 8.59(dd, 1H, 8.1 Hz, 1.5 Hz), 8.56(brs, 1H), 8.11(d, 2H, 8.8 Hz), 7.86(d, 2H, 8.4 Hz), 7.30(d, 1H, 8.8 Hz), 7.16(m, 1H), 7.07(dd, 1H, 8.1H, 1.5 Hz), 7.04(d, 1H, 2.6 Hz), 6.90(dd, 1H, 8.1 Hz, 1.5 Hz), 6.81(dd, 1H, 8.4 Hz, 2.6 Hz), 3.95(s, 3H), 1.70(s, 4H), 1.28(s, 6H), 1.25(s, 6H)

Polyphosphoric acid (2.2 g) was added to Compound 29 (111 mg, 0.238 mmol), and the mixture was stirred at 100° C. for 1 hour and 30 minutes. The reaction mixture was added with water and extracted with dichloromethane. After the organic layer was dried, the solvent was evaporated under reduced pressure and the resulting residue was purified by silica gel column chromatography (AcOEt:n-hexane=1:40) to give methyl 4-[2,3-(2,5-dimethyl-2,5-hexano)-dibenzo[b,f][1,4]oxazepine-11-yl]benzoate (Compound 30, 33.4 mg, 31%).

$^1$H-NMR CDCl$_3$ : 8.12(d, 2H, 8.4 Hz), 7.92(d, 2H, 8.8 Hz), 7.44(m, 1H), 7.21(m, 3H), 7.16(s, 1H), 7.01(s, 1H), 1.66(m, 4H), 1.30(s, 6H), 1.11(s, 6H)

Compound 30 (30.0 mg, 0.067 mmol) was suspended in ethanol (5 ml) and 2N sodium hydroxide (1 ml) and the suspension was stirred at room temperature for 40 minutes. The reaction mixture was acidified with 2N hydrochloric acid and then extracted with dichloromethane. The organic layer was washed with water and saturated brine. After dryness, the solvent was evaporated under reduced pressure to give the compound of the present invention: 4-[2,3-(2,5-dimethyl-2,5-hexano)dibenzo[b,f][1,4]oxazepine-11-yl-benzoic acid (HX620: Compound 31, 29.0 mg, 100%). The product was recrystallized from a mixture of ethanol/water top give purified compound. m.p.289° C.

$^1$H-NMR CDCl$_3$ 8.19(d, 2H, 8.8 Hz), 7.97(d, 2H, 8.8 Hz), 7.46(m, 1H), 7.22(m, 3H), 7.18(s, 1H), 7.02(s, 1H), 1.66(s, 4H), 1.31(s, 6H), 1.12(s, 6H)

Example 7
Preparation of 4-[2,3-(2,5-dimethyl-2,5-hexano)dibenzo[b,f][1,4]thiazepine-11-yl]benzoic acid (HX630)

1,2,3,4-Tetrahydro-1,1,4,4-tetramethylnaphthalene (6.0 g, 32.0 mmol) was added to chlorosulfonic acid (10 ml) at 0° C. and the mixture was stirred for 1 hour. The reaction mixture was poured into ice water and extracted with ethyl acetate. The organic phase was washed with saturated brine and dried, and then the solvent was evaporated under reduced pressure. The residue was added with zinc powder (10 g, 15.2 mmol) and ethanol (20 ml), and further added with concentrated hydrochloric acid (40 ml) over 5 minutes, and the mixture was heated to reflux for 1 hour and 25 minutes. The reaction was added with ice water and ethyl acetate and then extracted. The organic phase was washed with saturated brine and dried, and then the solvent was evaporated under reduced pressure to give a crude product (6.82 g).

$^1$H-NMR CDCl$_3$ : 3.37 (s, 1H, —SH)

DMSO (8 ml) was added to the above crude thiophenol compound (290 mg, 1.3 mmol), o-chloronitrobenzene (212 mg, 1.3 mmol), and potassium hydroxide (71.5 mg, 1.3 mmol), and the mixture was stirred at 100 ° C. for 15 hours and 40 minutes. The reaction mixture was added with water and dichloromethane and further added with concentrated hydrochloric acid (1 ml). The organic phase was washed with diluted hydrochloric acid and brine and dried, and then the solvent was evaporated under reduced pressure. The resulting residue was purified by silica gel column chromatography (AcOEt:n-hexane=1:40) to give s-(5,6,7,8-tetrahydro-5,5,8,8-tetramethyl-2-naphtalenyl)-2-nitrophenylthiophenol (Compound 32, 112.3 mg, 25%).

$^1$H-NMR CDCl$_3$ : 8.23(dd, 1H, 8.1 Hz, 1.5 Hz), 7.52(d, 1H, 1.8 Hz), 7.40(d, 1H, 8.1 Hz), 7.35(m, 1H), 7.29(dd, 1H, 8.1 Hz, 1.8 Hz), 7.20(m, 1H), 6.90(dd, 1H, 8.1 Hz, 1.1 Hz), 1.72(s, 4H), 1.32(s, 6H), 1.27(s, 6H)

Compound 32 (275.3 mg, 0.807 mmol) was suspended in water (5 ml) and ethanol (10 ml) and the mixture was added with concentrated hydrochloric acid (0.5 ml). The mixture was added with iron powder (210 mg) and then heated to reflux for 5 minutes. The reaction mixture was filtered to removed solid materials and the filtrate was extracted with ethyl acetate. The organic phase was washed with water and saturated brine and dried, and then the solvent was concentrated under reduced pressure. The residue was purified by silica gel column chromatography (AcOEt:n-hexane=1:40) to give s-(5,6,7,8-tetrahydro-5,5,8,8-tetramethyl-2-naphtalenyl)-2-aminothiophenol (Compound 33, 91.4 mg, 36%).

$^1$H-NMR CDCl$_3$ : 7.43(dd, 1H, 7.7 Hz, 1.5 Hz), 7.21(m, 1H), 7.14(d, 1H, 8.4 Hz), 7.10(d, 1H, 2.2 Hz), 6.77(m, 3H), 4.30(brs, 2H), 1.64(s, 4H), 1.22(s, 6H), 1.20(s, 6H)

Compound 33 (91.4 mg, 0.294 mmol) was dissolved in dried benzene (5 ml) and the mixture was added with pyridine (0.2 ml, 2.5 mmol). To this solution, terephthalic acid monomethyl ester chloride (76 mg, 0.38 mmol) was added and the mixture was stirred at room temperature for 18 hours. The reaction mixture was added with ice water and dilute hydrochloric acid and then extracted with ethyl acetate. The organic phase was dried and the solvent was evaporated to give a crude product (146.8 mg). This crude product was purified by silica gel column chromatography (AcOEt:n-hexane=1: 20 → 1:10) to give methyl 4-[2-(s-(5,6,7,8-tetrahydro-5,5,8,8-tetramethylnaphtalenyl)amino)carbamoyl]benzoate (compound 34, 123.7 mg, 89%).

$^1$H-NMR CDCl$_3$ : 9.03(brs, 1H), 8.65(d, 1H, 7.0 Hz), 8.05(d, 2H, 8.8 Hz), 7.66(dd, 1H, 7.7 Hz, 1.5 Hz), 7.63(d, 2H, 8.8 Hz), 7.51(m, 1H), 7.18(m, 3H), 7.10(d, 1H, 1.8 Hz), 6.83(dd, 1H, 8.4 Hz, 2.2 Hz), 3.95(s, 3H), 1.61(s, 4H), 1.20(s, 6H), 1.13(s, 6H)

Polyphosphoric acid (1.48 g) was added to Compound 34 (46.8 mg, 0.099 mmol) and the mixture was stirred at 120° C. for 45 minutes. The reaction mixture was added with water and extracted with dichloromethane. The organic phase was dried and the solvent was evaporated under reduced pressure. The residue was purified by silica gel column chromatography (AcOEt:n-hexane=1:40) to give methyl 4-[2,3-(2,5-dimethyl-2,5-hexano)dibenzo[b,f][1,4]thiazepine-11-yl]benzoate (Compound 35, 27.3 mg, 61%).

$^1$H-NMR CDCl$_3$ : 8.09(d, 2H, 8.4 Hz), 7.90(d, 2H, 8.4 Hz), 7.48(dd, 1H, 7.7 Hz, 1.5 Hz), 7.44(s, 1H), 7.38(d, 2H, 7.7 Hz), 7.34(m, 1H), 7.13(m, 1H), 7.03(s, 1H), 3.96(s, 3H), 1.64(m, 4H), 1.31(s, 3H), 1.28(s, 3H), 1.13(s, 3H), 1.06(s, 3H)

Compound 35 (26.4 mg, 0.058 mmol) was suspended in ethanol (5 ml) and sodium hydroxide (1 ml) and the mixture was stirred at room temperature for 40 minutes. The reaction mixture was acidified with 2N hydrochloric acid and the mixture was extracted with dichloromethane. The organic phase was washed with water and saturated brine and then dried, and the solvent was concentrated under reduced pressure to give the compound of the present invention: 4-[2,3-(2,5-dimethyl-2,5-hexano)dibenzo[b,f][1,4]-thiazepine-11-yl]benzoic acid (HX 630, Compound 36, 24.9 mg, 97%). The product was recrystallized from a mixture of ethanol/water to give purified compound. m.p.299° C.
$^1$H-NMR CDCl$_3$ : 8.17(d, 2H, 8.4 Hz), 7.94(d, 2H, 8.4 Hz), 7.48(dd, 1H, 7.7 Hz, 1.1 Hz), 7.45(s, 1H), 7.37(m, 2H), 7.13(m, 1H), 7.04(s, 1H), 1.65(m, 4H), 1.31(s, 3H), 1.28(s, 3H), 1.15(s, 3H), 1.07(s, 3H)

Example 8

Preparation of 4-[2,3-(2,5-dimethyl-2,5-hexano)-dibenzo[b,e]azepine-11-yl]benzoic acid (HX640)

5,6,7,8-tetrahydro-5,5,8,8-tetramethylnaphthalene (10.0 g, 53.2 mmol) and o-nitrobenzoic acid chloride (9.4 g, 50.5 mmol) were dissolved in dichloromethane (50 ml), and the mixture was added with AlCl$_3$ (14.3 g) portionwise and then heated under reflux for 1 hour and 30 minutes. The reaction mixture was poured into water and extracted with dichloromethane and dried, and then the solvent was evaporated to give a crude product (21.59 g). This product was purified by silica gel column chromatography (AcOEt:n-hexane=1:10) to give (5,5,8,8-tetramethyl-5,6,7,8- tetrahydro-2-naphthyl)carbonyl-2-nitrobenzene (Compound 37, 7.5 g, 42%). This product was further recrystallized from n-hexane.
$^1$H-NMR CDCl$_3$ : 8.23(d, 1H, 8.1 Hz), 7.84(s, 1H), 7.75(t, 1H, 6.2 Hz), 7.69(t, 1H, 7.0 Hz), 7.48(dd, 1H, 7.7 Hz, 1.5 Hz), 7.34(m, 2H), 1.69(s, 4H), 1.28(s, 6H), 1.26(s, 6H)

Compound 37 (262.1 mg, 0.78 mmol) was dissolved in ethanol (10 ml), and the solution was added with iron powder (313 mg) and concentrated hydrochloric acid (2.0 ml), and then heated under reflux for 15 minutes. The reaction mixture was filtered and the filtrate was added with ethyl acetate and extracted. The solvent was evaporated after dryness to give (5,5,8,8-tetramethyl-5,6,7,8-tetrahydro-2-naphthyl)carbonyl-2-aniline (Compound 38, 242.9 mg, 100%).
$^1$H-NMR CDCl$_3$ : 7.61(d, 1H, 1.8 Hz), 7.51(d, 1H, 8.1 Hz), 7.41(dd, 1H, 8.1 Hz, 1.8 Hz), 7.37(d, 1H, 8.1 Hz), 7.29(m, 1H), 6.74(d, 1H, 8.1 Hz), 6.61(t, 1H, 8.1 Hz), 1.72(s, 4H), 1.32(s, 6H), 1.29(s, 6H)

Compound 38 (67.3 mg, 0.22 mmol) was dissolved in diethyl ether (2 ml), and the solution was added with LiAlH$_4$ (41.3 mg, 1.09 mmol, suspended in 8 ml of diethyl ether) and heated under reflux for 19 hours. The reaction mixture was treated by a conventional manner and the resulting crude product was purified by silica gel column chromatography (AcOEt:n-hexane=1:40–1:20) to give 2-(5,6,7,8-tetrahydro-5,5,8,8-tetramethylnaphthylmethyl)aniline (Compound 39, 34.9 mg, 54%).
$^1$H-NMR CDCl$_3$ : 7.20(d, 1H, 8.1 Hz), 7.15(d, 1H), 7.09(m, 1H), 7.05(m, 1H), 6.89(dd, 1H, 8.1 Hz), 6.77(td, 1H, 7.7 Hz), 6.70(d, 1H, 7.7 Hz), 3.86(s, 3H), 3.70(brs, 2H), 1.66(s, 4H), 1.25(s, 6H), 1.24(s, 6H)

Compound 39 (88.5 mg, 0.30 mmol) was dissolved in dry benzene (4 ml) and the solution was added with pyridine (0.2 ml, 2.5 mmol). Terephthalic acid monomethyl ester chloride (73.7 mg, 0.37 mmol) was added to this solution, and the reaction mixture was stirred at room temperature for 1 hour and 30 minutes. The reaction mixture was added with ice water and 2N HCl and then extracted with ethyl acetate and dried, and then the solvent was evaporated and the residue was purified by silica gel column chromatography to give methyl 4-[2-(2-(5,6,7,8-tetrahydro-5,5,8,8-tetramethylnaphthylmethyl )aminocarbonyl]benzoate (Compound 40, 115.1 mg, 84%).
$^1$H-NMR CDCl$_3$ : 8.13(d, 1H, 8 Hz), 7.99(d, 2H, 8.4 Hz), 7.62(brs, 1H), 7.38(d, 2H, 8.4 Hz), 7.30(m, 3H), 7.21(t, 1H, 7.7 Hz), 7.11(d, 1H), 6.90(dd, 1H, 8.1 Hz), 4.04(s, 2H), 3.95(s, 3H), 1.68(m, 4H), 1.29(s, 6H), 1.15(s, 6H)

Polyphosphoric acid (1.56 g) was added to Compound 40 (103.4 mg, 0.227 mmol) and the mixture was stirred at 110° C. for 45 minutes. The reaction mixture was added with water and extracted with dichloromethane. The organic phase was dried and the solvent was evaporated, and the resulting residue was purified by silica gel column chromatography (AcOEt:n-hexane=1:20) to give methyl 4-[2,3-(2,5-dimethyl-2,5-hexano)dibenzo[b,e]azepine-11-yl]benzoate (Compound 41, 78.3 mg, 79%).
$^1$H-NMR CDCl$_3$ : 8.11(d, 2H, 8.4 Hz), 7.96(d, 2H, 8.4 Hz), 7.43(brd, 1H, 8 Hz), 7.25(m, 2H), 7.22(s, 1H), 7.17(t, 1H, 7.3 Hz), 7.08(s, 1H), 3.96(s, 3H), 3.70(brs, 1H), 3.67(brs, 1H), 1.64(brs, 4H), 1.40(brs, 3H), 1.30(brs, 3H), 1.15(brs, 3H), 1.04(brs, 3H)

Compound 41 (78.3 mg, 0.179 mmol) was suspended in a mixture of ethanol (10 ml) and 2N NaOH (2 ml) and the suspension was stirred at room temperature for 1 hour. The reaction mixture was acidified with 2N HCl and then extracted with dichloromethane. The organic phase was dried and the solvent was evaporated to give 4-[2,3-(2,5-dimethyl-2,5-hexano)dibenzo[b,e]azepine-11-yl]benzoic acid (HX640, Compound 42, 73.6 mg, 97%). The product was recrystallized from a mixture of ethanol/water to give purified compound. m.p.>300° C.
$^1$H-NMR DMSO-d$_6$ (120° C.): 8.05(d, 2H, 8.4 Hz), 7.89(d, 2H, 8.4 Hz), 7.39(s, 1H), 7.33(m, 2H), 7.26(td, 1H, 7.3 Hz, 1.5 Hz), 7.16(td, 7.3 Hz, 1.5 Hz), 7.09(s, 1H), 3.69(s, 2H), 1.66(m, 4H), 1.32(s, 6H), 1.11(s, 6H)
Anal. Calc. for C$_{29}$H$_{29}$NO$_2$ C:82.24, H:6.90, N:3.31; Found C:82.30, H: 6.98, N:3.02

Example 9

Preparation of 4-[1,3-dihydro-7,8-(2,5- dimethyl-2,5-hexano)-2-oxo-2H-1,4-benzodiazepine-5-yl]benzoic acid (HX800)

1,2,3,4-Tetrahydro-1,1,4,4-tetramethylnaphthalene (10.0 g, 53.2 mmol) and terephthalic acid monomethyl ester chloride (10.0 g, 50.5 mmol) were dissolved in dichloromethane (50 ml) and the mixture was added with AlCl$_3$ (14.3 g, 107.5 mmol) over 10 minutes under ice cooling. After reflux for 1 hour, the reaction mixture was poured into ice water and extracted with ethyl acetate. The organic phase was washed with water and saturated brine and dried, and then concentrated to give methyl 4-[(5,5,8,8-tetramethyl-5,6,7,8-tetrahydro-2-naphthyl)carbonyl]benzoate (Compound 43, 18.5 g, 99%). A part of the product was recrystallized from ethyl acetate.
$^1$H-NMR CDCl$_3$ : 8.15(d, 2H, 8.8 Hz), 7.83(d, 2H, 8.4 Hz), 7.79(d, 1H, 1.8 Hz), 7.54(dd, 1H, 8.1 Hz, 1.8 Hz), 7.41(d, 1H, 8.4 Hz), 3.97(s, 3H), 1.72(s, 4H), 1.32(s, 6H), 1.29(s, 6H)

Compound 43 (693 mg, 1.98 mmol) was dissolved in concentrated H$_2$SO$_4$ (5 ml) and the mixture was added with KNO$_3$ (240 mg, 2.37 mmol) under ice cooling. After 1 hour, the reaction mixture was poured into ice water and extracted with dichloromethane. The organic phase was washed with saturated aqueous solution of sodium hydrogen carbonate, water and saturated brine, and then concentrated after dryness. The residue was recrystallized from ethyl acetate to give methyl 4-[3-nitro-5,5,8,8-tetramethyl-5,6,7,8-tetrahydro-2-naphthylcarbonyl]benzoate as colorless needles (Compound 44, 414 mg, 53%).

$^1$H-NMR CDCl$_3$ : 8.16(s, 1H), 8.11(d, 2H, 8.4 Hz), 7.81(d, 2H, 8.4 Hz), 7.38(s, 1H), 3.94(s, 3H), 1.77(s, 4H), 1.39(s, 6H), 1.31(s, 6H)

Compound 45 (318.5 mg, 0.806 mmol) was suspended in water (5 ml) and ethanol (10 ml) and the suspension was added with concentrated hydrochloric acid (1.0 ml). The mixture was added with iron powder (317 mg) and heated under reflux for 50 minutes, and then the reaction mixture was filtered to remove solid materials. The filtrate was extracted with ethyl acetate, and the organic phase was washed with water and saturated brine and dried, and then the organic phase was concentrated to give methyl 4-[3-amino-5,5,8,8-tetramethyl-5,6,7,8-tetrahydro-2-naphthyl)carbonyl]benzoate as yellow crystals (Compound 46, 279.2 mg, 95%).

$^1$H-NMR CDCl$_3$ : 8.14(d, 2H, 8.4 Hz), 7.69(d, 2H, 8.8 Hz), 7.31(s, 1H), 6.67(s, 1H), 5.90(brs, 2H), 3.97(s, 3H), 1.65(m, 4H), 1.28(s, 6H), 1.11(s, 6H)

Pyridine (5 ml) was added to Compound 46 (70 mg, 0.19 mmol) and glycine methyl ester hydrochloride (38.3 mg, 0.31 mmol) and the mixture was heated under reflux for 16 hours. The reaction mixture was added with diluted hydrochloric acid and extracted with dichloromethane. The organic phase was washed with water and saturated brine and dried, and then concentrated to give a residue (72.3 mg). The residue was purified by silica gel column chromatography (AcOEt:n-hexane=1:4) to give methyl 4-[1,3-dihydro-7,8-(2,5-dimethyl-2,5-hexano)-2-oxo-2H-1,4-benzodiazepine-5-yl]benzoate (Compound 47, 34.7 mg, 45%). The starting material (23.1 mg) was also recovered (33%).

$^1$H-NMR CDCl$_3$ : 8.06(d, 2H, 8.8 Hz), 7.66(m, 3H), 7.16(s, 1H), 6.96(s, 1H), 4.36(brs, 2H), 3.95(s, 3H), 1.70(m, 4H), 1.33(s, 6H), 1.16(s, 6H)

Compound 47 (32.6 mg, 0.08 mmol) was suspended in ethanol (5 ml) and 2N NaOH (1 ml) and the mixture was stirred at room temperature for 20 minutes. The reaction mixture was acidified with 2N hydrochloric acid and extracted with dichloromethane. The organic layer was washed with water and saturated brine and dried, and then concentrated to give 4-[1,3-dihydro-7,8-(2,5-dimethyl-2,5-hexano)-2-oxo-2H-1,4-benzodiazepine-5-yl]benzoic acid (HX800, Compound 48, 26.0 mg, 83%). A part of the product was recrystallized from methanol/hexane. m.p.>300° C.

MS M$^+$390

$^1$H-NMR CDCl$_3$ : 8.23(brs, 1H), 8.12(d, 2H, 8.4 Hz), 7.69(d, 2H, 8.4 Hz), 7.17(s, 1H), 7.01(s, 1H), 4.38(brs, 2H), 1.71(s, 4H), 1.34(s, 6H), 1.17(s, 6H)

Example 10

Preparation of 4-[1,3-dihydro-7,8-(2,5-dimethyl-2,5-hexano)-1-methyl-2-oxo-2H-1,4-benzodiazepine-5-yl] benzoic acid (HX801)

NaH (60% in oil, 7.1 mg, 0.18 mmol, 2 eq) was washed with hexane and dried, and then methyl 4-[1,3-dihydro-7,8-(2,5-dimethyl-2,5-hexano)-2-oxo-2H-1,4-benzodiazepine-5-yl]benzoate (36 mg, 0.089 mmol) obtained in Example 9 was dissolved in DMF (4 ml) and added to the base. This mixture was stirred at room temperature for 10 minutes, and after the addition of CH$_3$I (0.02 ml, 0.36 mmol, 4 eq), stirring was continued for 2 hours and 30 minutes. The reaction mixture was poured into ice water and extracted with dichloromethane. The organic phase was washed with water and saturated brine and then concentrated after dryness. The residue was purified by silica gel column chromatography (AcOEt:n-hexane=1:1) to give methyl 4-[1,3-dihydro-7,8-(2,5-dimethyl-2,5-hexano)-1-methyl-2-oxo-2H-1,4-benzodiazepine-5-yl]benzoate (Compound 49, 21.8 mg, 59%).

$^1$H-NMR CDCl$_3$ : 8.07(d, 2H, 8.4 Hz), 7.74(d, 2H, 8.4 Hz), 7.21(s, 1H), 7.13(s, 1H), 4.82(d, 1H, 10.3 Hz), 3.95(s, 3H), 3.86(d, 1H, 10.6 Hz), 3.40(s, 3H), 1.71(m, 4H), 1.38(s, 3H), 1.31(s, 3H), 1.20(s, 3H), 1.14(s, 3H)

Compound 49 (29.6 mg, 0.07 mmol) was suspended in ethanol (3 ml) and 2N NaOH (1 ml) and the suspension was stirred at room temperature for 40 minutes. The reaction mixture was acidified with 2N HCl and extracted with dichloromethane. The organic phase was washed with water and saturated brine and dried, and then concentrated to give 4-[1,3-dihydro-7,8-(2,5-dimethyl-2,5-hexano)-1-methyl-2-oxo-2H-1,4-benzodiazepine-5-yl]benzoic acid (HX801, Compound 50, 23.5 mg, 83%). A part of the product was recrystallized from ethyl acetate/hexane. m.p.>300° C.

$^1$H-NMR CDCl$_3$ : 8.13(d, 2H, 8.8 Hz), 7.77(d, 2H, 8.4 Hz), 7.22(s, 1H), 7.14(s, 1H), 4.84(d, 1H, 10.6 Hz), 3.88(d, 1H, 10.6 Hz), 3.41(s, 3 Hz), 1.72(m, 4H), 1.39(s, 3H), 1.32(s, 3H), 1.21(s, 3H), 1.15(s, 3H)

Anal. Calc. for C$_{25}$H$_{28}$N$_2$O$_3$ C:74.23, H:6.98, N:6.93; Found C:74.19, H:6.97, N:6.63

Example 11

Preparation of 4-[3(S)-methyl-1,3-dihydro-7,8-(2,5-dimethyl-2,5-hexano)-2-oxo-2H-1,4-benzodiazepine-5-yl] benzoic acid (HX810)

Pyridine (5 ml) was added to methyl 4-[3-amino-5,5,8,8-tetramethyl-5,6,7,8-tetrahydro-2-naphthyl)carbonyl] benzoate (188 mg, 0.515 mmol) obtained in Example 9 and L-alanine ethyl ester hydrochloride (177 mg, 0.77 mmol, 1.5 eq) and the mixture was refluxed for 16 hours. The reaction mixture was added with diluted hydrochloric acid and extracted with dichloromethane. The organic phase was washed with water and saturated brine, and then concentrated after dryness. The residue was purified by silica gel column chromatography (AcOEt:n-hexane=1:3) to give methyl 4-[3(S)-methyl-1,3-dihydro-7,8-(2,5-dimethyl-2,5-hexano)-2-oxo-2H-1,4-benzodiazepine-5-yl]benzoate (Compound 51, 25.6 mg, 12%).

$^1$H-NMR CDCl$_3$ : 8.06(d, 2H, 8.4 Hz), 7.67(d, 2H, 8.4 Hz), 7.17(s, 1H), 6.97(s, 1H), 3.94(s, 3H), 3.84(q, 1H, 6.6 Hz), 1.74(d, 3H, 6.6 Hz), 1.71(m, 4H), 1.34(s, 3H), 1.31(s, 3H), 1.19(s, 3H), 1.12(s, 3H)

Compound 51 (15.1 mg, 0.036 mmol) was suspended in ethanol (3 ml) and 2N NaOH (1 ml) and the suspension was stirred at room temperature for 40 minutes. The reaction mixture was acidified with 2N HCl and extracted with dichloromethane. The organic layer was washed with water and saturated brine and dried, and then concentrated to give 4-[3(S)-methyl-1,3-dihydro-7,8-(2,5-dimethyl-2,5-hexano)-2-oxo-2H-1,4-benzodiazepine-5-yl]benzoic acid (HX810, Compound 52, 14.9 mg, 100%). A part of the product was recrystallized from ethyl acetate/hexane. m.p.>300° C.

$^1$H-NMR CDCl$_3$ : 8.11(d, 2H, 8.4 Hz), 7.95(brs, 1H), 7.70(d, 2H, 8.4 Hz), 7.18(s, 1H), 7.00(s, 1H), 3.85(q, 1H, 6.6 Hz), 1.75(d, 3H, 6.6 Hz), 1.71(m, 4H), 1.35(s, 3H), 1.32(s, 3H), 1.20(s, 3H), 1.13(s, 3H)

Anal. Calc. for C$_{25}$H$_{28}$N$_2$O$_3$ C:74.23, H:6.98, N:6.93; Found C:74.19, H:7.18, N:6.66

Example 12

Preparation of 4-[1,3-dihydro-7,8-(2,5-dimethyl-2,5-hexano)-1-isopropyl-2-oxo-2H-1,4-benzodiazepine-5-yl] benzoic acid (HX803)

NaH (60% in oil, 4.7 mg, 0.12 mmol, 2 eq) was washed with hexane and dried, and then methyl 4-[1,3-dihydro-7,8-(2,5-dimethyl-2,5-hexano)-2-oxo-2H-1,4-benzodiazepine-5-yl]benzoate (24 mg, 0.059 mmol) obtained in Example 9 was dissolved in DMF (6 ml) and then added to the base. The reaction mixture was stirred at room temperature for 15 minutes, and after 2-iodopropane (0.02 ml, 0.24 mmol, 4 eq) was added to the mixture, stirring was further continued for 4 hours. The reaction mixture was poured into ice water and extracted with dichloromethane, and the extract was washed with water and saturated brine and concentrated after dryness. The residue was purified by silica gel column chromatography (AcOEt:n-hexane=1:5) to give methyl 4-[1,3-dihydro-7,8-(2,5-dimethyl-2,5-hexano)-1-isopropyl-2-oxo-2H-1,4-benzodiazepine-5-yl]benzoate (Compound 53, 6.4 mg, 24%).

$^1$H-NMR CDCl$_3$ : 8.07(d, 2H, 8.4 Hz), 7.74(d, 2H, 8.4 Hz), 7.31(s, 1H), 7.10(s, 1H), 4.73(d, 1H, 10.3 Hz), 4.57(septet, 1H, 7.0 Hz), 3.95(s, 3H), 3.83(d, 1H, 10.3 Hz), 1.72(m, 4H), 1.52(d, 3H, 6.6 Hz), 1.38(s, 3H), 1.32(s, 3H), 1.21(s, 3H), 1.18(d, 3H, 7.0 Hz), 1.13(s, 3H)

Compound 53 (6.4 mg, 0.014 mmol) was suspended in ethanol (4 ml) and 2N NaOH (0.5 ml) and the mixture was stirred at room temperature for 2 hours. The reaction mixture was acidified with 2N HCl and extracted with dichloromethane. The organic phase was washed with water and saturated brine and dried, and then concentrated to give 4-[1,3-dihydro-7,8-(2,5-dimethyl-2,5-hexano)-1-isopropyl-2-oxo-2H-1,4-benzodiazepine-5-yl]benzoic acid (HX803, Compound 54, 6.2 mg, 100%). A part of the product was recrystallized from ethyl acetate/hexane. m.p. 275° C.

$^1$H-NMR CDCl$_3$ : 8.13(d, 2H, 8.4 Hz), 7.78(d, 2H, 8.1 Hz), 7.32(s, 1H), 7.11(s, 1H), 4.77(d, 1H, 10.3 Hz), 4.58(septet, 1H, 7.0 Hz), 3.85(d, 1H, 10.3 Hz), 1.73(m, 4H), 1.53(d, 3H, 7.0 Hz), 1.39(s, 3H), 1.32(s, 3H), 1.22(s, 3H), 1.19(d, 3H, 7.3 Hz), 1.14(s, 3H)

Example 13

Preparation of 4-[1-benzyl-1,3-dihydro-7,8-(2,5-dimethyl-2,5-hexano)-2-oxo-2H-1,4-benzodiazepine-5-yl)benzoic acid (HX805)

NaH (60% in oil, 6.1 mg, 0.15 mmol, 2 eq) was washed with hexane and dried, and then methyl 4-[1,3-dihydro-7,8-(2,5-dimethyl-2,5-hexano)-2-oxo-2H-1,4-benzodiazepine-5-yl]benzoate (31.9 mg, 0.076 mmol) obtained in Example 9 was dissolved in DMF (3 ml) and then added to the base. The reaction mixture was stirred at room temperature for 20 minutes, and after benzyl bromide (0.035 ml, 0.30 mmol, 4 eq) was added to the mixture, stirring was further continued for 1 hour. The reaction mixture was poured into ice water and extracted with dichloromethane. The organic phase was washed with water and saturated brine, and then concentrated after dryness. The residue was recrystallized from ethyl acetate/dichloro methane to give methyl 4-[1-benzyl-1,3-dihydro-7,8-(2,5-dimethyl-2,5-hexano)-2-oxo-2H-1,4-benzodiazepine-5-yl]benzoate (Compound 55, 23.3 mg, 60%).

$^1$H-NMR CDCl$_3$ : 8.03(d, 2H, 8.4 Hz), 7.51(d, 2H, 8.4 Hz), 7.25(s, 1H), 7.16(m, 3H), 7.06(m, 2H), 4.89(d, 1H, 10.3 Hz), 4.87(d, 1H, 15.4 Hz), 3.97(d, 1H, 10.3 Hz), 3.95(s, 3H), 1.66(s, 4H), 1.23(s, 3H), 1.20(s, 3H), 1.11(s, 3H), 1.08(s, 3H)

Compound 55 (19.1 mg, 0.035 mmol) was suspended in ethanol (6 ml) and 2N NaOH (1 ml) and the suspension was stirred at 70° C. for 2 hours. The reaction mixture was acidified with 2N HCl and extracted with dichloromethane. The organic phase was washed with water and saturated brine and dried, and then concentrated to give 4-[1-benzyl-1,3-dihydro-7,8-(2,5-dimethyl-2,5-hexano)-2-oxo-2H-1,4-benzodiazepine-5-yl]benzoic acid (HX805, Compound 56, 12.5 mg, 72%). A part of the product was recrystallized from ethyl acetate/dichloromethane. m.p.>300 ° C.

$^1$H-NMR CDCl$_3$ : 8.08(d, 2H, 8.8 Hz), 7.55(d, 2H, 8.4 Hz), 7.16(m, 3H), 7.07(m, 2H), 7.00(s, 1H), 5.45(d, 1H, 14.7 Hz), 4.91(d, 1H, 10.3 Hz), 4.88(d, 1H, 14.3 Hz), 3.99(d, 1H, 10.3 Hz), 1.65(m, 4H), 1.23(s, 3H), 1.21(s, 3H), 1.12(s, 3H), 1.09(s, 3H)Anal. Calc. for C$_{31}$H$_{32}$N$_2$O$_3$ C: 77.47, H:6.71, N:5.83; Found C:77.27, H:6.80, N:5.70

Example 14

Preparation of 4-[3(S)-benzyl-1,3-dihydro-7,8-(2,5-dimethyl-2,5-hexano)-2-oxo-2H-1,4-benzodiazepine-5-yl] benzoic acid (HX850)

SOCl$_2$ (4 ml) was added to Fmoc-(L)-phenylalanine (272 mg, 0.70 mmol) and the mixture was refluxed for 30 minutes. The SOCl$_2$ was evaporated under reduced pressure and the residue was well dried. The residue was added with methyl 4-[3-amino-5,5,8,8-tetramethyl-5,6,7,8-tetrahydro-2-naphthylcarbonyl]benzoate (89 mg, 0.244 mmol) and DMAP (12 mg), and further added with anhydrous benzene (10 ml) and pyridine (0.5 ml). This mixture was stirred at room temperature for 50 minutes, acidified with 2N HCl, and then extracted with dichloromethane. The organic phase was washed with water and saturated brine and dried over Na$_2$SO$_4$, and then concentrated. The residue was purified by silica gel column chromatography (AcOEt:n-hexane=1:30) to give methyl 4-[[3-N-(N-α-9-fluorenylmethoxycarbonyl-L-phenylalanyl)amide-5,5,8,8-tetrahydro-2-naphthyl]carbonyl]benzoate (Compound 57, 117.8 mg, 99%).

$^1$H-NMR CDCl$_3$ : 11.14(s, 1H), 8.61(s, 1H), 8.08(d, 2H, 8.1 Hz), 7.75(d, 2H, 7.3 Hz), 7.62(m, 3H), 7.52(m, 2H), 7.40(m, 3H), 7.24(m, 5H), 7.11(d, 1H), 5.43(d, 1H), 4.65(d, 1H), 4.39(m, 1H), 4.37(m, 1H), 4.19(m, 1H), 3.97(s, 3H), 3.28(m, 1H), 3.19(m, 1H), 1.70(m, 4H), 1.36(s, 6H), 1.14(s, 6H)

A mixture of Compound 57 (82.3 mg, 0.11 mmol) added with dichloromethane (4 ml) and piperidine (1 ml) was stirred at room temperature for 40 minutes. The solvent was evaporated under reduced pressure and the residue was dried. The residue was then added with butanol (10 ml) and acetic acid (0.5 ml) and the mixture was stirred at 80° C. for 2 hours. The reaction mixture was added with aqueous solution of sodium hydrogen carbonate and then extracted with dichloromethane. The extract was purified by silica gel column chromatography (AcOEt:n-hexane=1:10) to give methyl 4-[3(S)-benzyl-1,3-dihydro-7,8-(2,5-dimethyl-2,5-hexano)-2-oxo-2H-1,4-benzodiazepine-5-yl]benzoate (Compound 58, 48.4 mg, 92%).

$^1$H-NMR CDCl$_3$ : 8.38(brs, 1H), 8.03(d, 2H, 8.4 Hz), 7.58(d, 2H, 8.4 Hz), 7.42(d, 2H, 7.3 Hz), 7.32(t, 2H, 7.3 Hz), 7.23(t, 1H, 7.0 Hz), 7.10(s, 1H), 7.00(s, 1H), 3.93(s, 3H), 3.87(m, 1H), 3.63(m, 2H), 1.68(m, 4H), 1.34(s, 3H), 1.31(s, 3H), 1.16(s, 3H), 1.10(s, 3H)

Compound 58 (28.6 mg, 0.06 mmol) was suspended in ethanol (5 ml) and 1N KOH (2 ml) and the mixture was stirred at room temperature for 30 minutes. The reaction mixture was acidified with 2N HCl and extracted with dichloromethane. The organic phase was dried and concentrated to give 4-[3(S)-benzyl-1,3-dihydro-7,8-(2,5-dimethyl-2,5-hexano)-2-oxo-2H-1,4-benzodiazepine-5-yl] benzoic acid (HX850, Compound 59, 24.8 mg, 89%). A part of the product was recrystallized from dichloromethane/hexane.

$^1$H-NMR CDCl$_3$ : 8.27(brs, 1H), 8.09(d, 2H, 8.1 Hz), 7.62(d, 2H, 8.1 Hz), 7.42(d, 2H, 7.3 Hz), 7.33(t, 2H, 8.1 Hz), 7.23(t, 1H), 7.13(s, 1H), 6.98(s, 1H), 3.87(m, 1H), 3.62(m, 2H), 1.69(m, 4H), 1.34(s, 3H), 1.31(s, 3H), 1.18(s, 3H), 1.11(s, 3H)

Example 15

Test Example

The effects of the compounds of the above Examples 1 and 2 on cell differentiation induced by retinoids were studied. As retinoid compounds (i.e., agonists against the all-trans retinoic acid receptor), retinoic acid and Am80 (4-[(5,6,7,8-tetrahydro-5,5,8,8-tetramethyl-2-naphthalenyl) carbamoyl]benzoic acid) were used. Cell differentiation inducing activities of the above retinoids on promyelocytic leukemia cell strain HL-60 were measured in the presence and absence of the compounds of Examples 1 and 2 according to the method described in the Japanese Patent Unexamined Publication (KOKAI) No.(Sho)61-76440/1986. The degrees of the differentiation into granulocytic cell were determined by observing nuclear morphologies and measuring abilities to reduce nitroblue tetrazolium (NBT). This method is well known in the art as a test that enables accurate evaluation of the cell differentiation inducing activity of retinoids. The results are shown in the Table 2 set out below (in the table, NTB positive ratio represents a percent value of differentiated cells based on living cells).

TABLE 2

| Retinoid (M) | Test compound (M) | NBT positive ratio (%) |
|---|---|---|
| Retinoic acid | Absent | 14 |
| $(1.1 \times 10^{-9})$ | HX600 $1.1 \times 10^{-7}$ | 68 |
| | HX600 $3.3 \times 10^{-7}$ | 76 |
| | HX600 $1.0 \times 10^{-6}$ | 69 |
| Retinoic acid | Absent | 36 |
| $(3.3 \times 10^{-9})$ | HX600 $1.1 \times 10^{-7}$ | 86 |
| | HX600 $3.3 \times 10^{-7}$ | 90 |
| | HX600 $1.0 \times 10^{-6}$ | 90 |
| Retinoic acid | Absent | 54 |
| $(1.0 \times 10^{-8})$ | HX600 $1.1 \times 10^{-7}$ | 91 |
| | HX600 $3.3 \times 10^{-7}$ | 91 |
| | HX600 $1.0 \times 10^{-6}$ | 91 |
| Am80 | Absent | 15 |
| $(3.7 \times 10^{-10})$ | HX600 $1.0 \times 10^{-9}$ | 21 |
| | HX600 $1.0 \times 10^{-8}$ | 41 |
| | HX600 $1.0 \times 10^{-7}$ | 72 |
| | HX600 $1.0 \times 10^{-6}$ | 67 |
| Am80 | Absent | 44 |
| $(1.1 \times 10^{-9})$ | HX600 $1.0 \times 10^{-9}$ | 48 |
| | HX600 $1.0 \times 10^{-8}$ | 65 |
| | HX600 $1.0 \times 10^{-7}$ | 90 |
| | HX600 $1.0 \times 10^{-6}$ | 93 |
| Am80 | Absent | 53 |
| $(3.3 \times 10^{-9})$ | HX600 $1.0 \times 10^{-9}$ | 64 |
| | HX600 $1.0 \times 10^{-8}$ | 73 |
| | HX600 $1.0 \times 10^{-7}$ | 93 |
| | HX600 $1.0 \times 10^{-6}$ | 93 |
| Am80 | Absent | 55 |
| $(1.0 \times 10^{-8})$ | HX600 $1.0 \times 10^{-9}$ | 69 |
| | HX600 $1.0 \times 10^{-8}$ | 80 |
| | HX600 $1.0 \times 10^{-7}$ | 91 |
| | HX600 $1.0 \times 10^{-6}$ | 95 |
| Am80 | Absent | 44 |
| $(3.3 \times 10^{-10})$ | HX640 $1.0 \times 10^{-10}$ | 44 |
| | HX640 $1.0 \times 10^{-9}$ | 46 |
| | HX640 $1.0 \times 10^{-8}$ | 75 |
| | HX640 $1.0 \times 10^{-7}$ | 89 |
| | HX640 $1.0 \times 10^{-6}$ | 85 |
| Am80 | Absent | 7 |
| $(1.1 \times 10^{-10})$ | HX640 $1.0 \times 10^{-10}$ | 7 |
| | HX640 $1.0 \times 10^{-9}$ | 5 |
| | HX640 $1.0 \times 10^{-8}$ | 24 |
| | HX640 $1.0 \times 10^{-7}$ | 69 |
| Am80 | Absent | 21 |
| $(3.7 \times 10^{-10})$ | LE135 $1.1 \times 10^{-7}$ | 3 |
| | LE135 $3.3 \times 10^{-7}$ | 1.2 |
| | LE135 $1.0 \times 10^{-6}$ | 1.3 |
| Am80 | Absent | 35 |

TABLE 2-continued

| Retinoid (M) | Test compound (M) | NBT positive ratio (%) |
|---|---|---|
| $(1.1 \times 10^{-9})$ | LE135 $1.1 \times 10^{-7}$ | 23 |
| | LE135 $3.3 \times 10^{-7}$ | 5 |
| | LE135 $1.0 \times 10^{-6}$ | 2 |
| Am80 | Absent | 51 |
| $(3.3 \times 10^{-9})$ | LE135 $1.1 \times 10^{-7}$ | 54 |
| | LE135 $3.3 \times 10^{-7}$ | 32 |
| | LE135 $1.0 \times 10^{-6}$ | 14 |
| Am80 | Absent | 55 |
| $(1.0 \times 10^{-8})$ | LE135 $1.1 \times 10^{-7}$ | 62 |
| | LE135 $3.3 \times 10^{-7}$ | 51 |
| | LE135 $1.0 \times 10^{-6}$ | 34 |

When the compounds of the present invention coexisted with retinoic acid or Am80, the ratios of the differentiated cells were remarkably increased, which apparently shows that the compounds of the present invention significantly enhance the cell differentiation inducing activities of retinoic acid and Am80. On the other hand, Compound LE135 used as control is known as an antagonist of retinoid (Compound No. 16 disclosed in Eyrolles, L., et al., J. Med. Chem., 37, pp.1508–1517, 1994: 4-(5H-7,8,9,10-tetrahydro-5,7,7,10, 10-pentamethylbenzo[e]naphto[2,3-b][1,4]diazepin-13-yl) benzoic acid) and corresponding to a structural isomer of Compound HX600 of the present invention. When this compound coexisted with Am80, the cell differentiation inducing activity of Am80 was significantly suppressed.

Example 16

Test Example

Effect of the compound of Example 10 (HX801) on the cell differentiation inducing activity by a retinoid was examined. Am80 was used as the retinoid compound and the cell differentiation inducing activity of the above retinoid on promyelocytic leukemia cell strain HL-60 was determined in the presence or absence of the compound of HX801 in the same manner as Example 15. The results are shown in the Table 3 set out below (in the table, the symbol "-" indicates no addition). When the compound of the present invention coexisted with Am80, the ratios of the differentiated cells were remarkably increased, which clearly indicates that the cell differentiation inducing activity of Am80 was enhanced by the compound of the present invention.

TABLE 3

| Am80 (M) | HX801 (M) | NBT Positive ratio (%) |
|---|---|---|
| — | — | 1 * |
| $1.0 \times 10^{-9}$ | — | 48 |
| $3.3 \times 10^{-10}$ | — | 30 |
| $1.1 \times 10^{-10}$ | — | 5 |
| $3.7 \times 10^{-11}$ | — | 3 |
| $1.2 \times 10^{-11}$ | — | 0.6 |
| — | $1.0 \times 10^{-6}$ | 1.1 |
| — | $3.3 \times 10^{-7}$ | 0.3 |
| — | $1.1 \times 10^{-7}$ | 1.1 |
| $1.0 \times 10^{-9}$ | $1.0 \times 10^{-6}$ | 77 |
| " | $3.3 \times 10^{-7}$ | 76 |
| " | $1.1 \times 10^{-7}$ | 63 |
| $3.3 \times 10^{-10}$ | $1.0 \times 10^{-6}$ | 71 |
| " | $3.3 \times 10^{-7}$ | 55 |
| " | $1.1 \times 10^{-7}$ | 49 |
| $1.1 \times 10^{-10}$ | $1.0 \times 10^{-6}$ | 48 |
| " | $3.3 \times 10^{-7}$ | 28 |
| " | $1.1 \times 10^{-7}$ | 22 |
| $3.7 \times 10^{-11}$ | $1.0 \times 10^{-6}$ | 4.4 |
| " | $3.3 \times 10^{-7}$ | 2.3 |
| " | $1.1 \times 10^{-7}$ | 4 |

TABLE 3-continued

| Am80 (M) | HX801 (M) | NBT Positive ratio (%) |
|---|---|---|
| $1.2 \times 10^{-11}$ | $1.0 \times 10^{-6}$ | 2 |
| " | $3.3 \times 10^{-7}$ | 2 |
| " | $1.1 \times 10^{-7}$ | 1.4 |

* Control

From the foregoing descriptions, it will be readily understood that the compounds of the present invention enhance the action of retinoids including retinoic acid and are useful as medicaments such as an agent enhancing retinoid actions.

What is claimed is:

1. A compound or a salt thereof represented by the following formula (I):

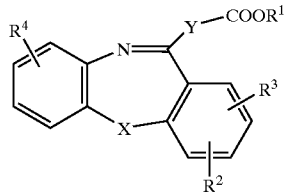

or represented by the following formula (II):

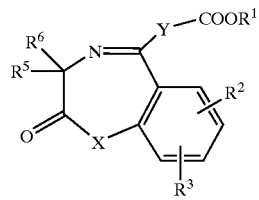

wherein, $R^1$ represents hydrogen atom or a $C_{1-6}$ alkyl group; $R^2$ and $R^3$ independently represent a hydrogen atom or a $C_{1-6}$ alkyl group, or $R^2$ and $R^3$ may combine together with the carbon atoms of the phenyl ring to which $R^2$ and $R^3$ bind to represent a 5- or 6-membered cycloalkyl group which may optionally be substituted with one or more $C_{1-4}$ alkyl groups; $R^4$ represents a hydrogen atom, a $C_{1-6}$ alkyl group, a $C_{1-6}$ alkoxy group, hydroxyl group, nitro group, or a halogen atom; $R^5$ represents a hydrogen atom, a $C_{1-6}$ alkyl group, or an aryl-substituted $C_{1-6}$ alkyl group; $R^6$ represents a hydrogen atom or a $C_{1-6}$ alkyl group; X represents —S—; and Y represents a phenylene group.

2. A medicament comprising a pharmaceutical composition including a compound of claim 1 or a physiologically acceptable salt of the claim 1, and a pharmaceutically acceptable additive.

3. A method of treatment of a disease selected from the group of vitamin A deficiency disease, hyperkeratosis of epithelial tissue, rheumatism, delayed allergy, and leukemia, the method comprising the steps of:
   subjecting a physiologically active retinoid substance to coexistence with the compound of claim 1, or a physiologically acceptable salt thereof; and
   enhancing the activity of the physiologically active retinoid which exhibits physiological activity by binding to an intranuclear receptor that belongs to the intranuclear receptor super family.

4. A pharmaceutical composition comprising a compound of claim 1 or a physiologically acceptable salt thereof together with a retinoid compound.

5. A method of treatment of a disease selected from the group of vitamin A deficiency disease, hyperkeratosis of epithelial tissue, rheumatism, delayed allergy, and leukemia by enhancing physiological activity of a physiologically active retinoid, wherein the physiologically active retinoid exhibits the physiological activity by binding to an intranuclear receptor that belongs to the intranuclear receptor super family, the method comprising the steps of:
   administering to a mammal a compound of claim 1 or a physiologically acceptable salt thereof; and
   enhancing the physiologic activity of the physiologically active retinoid substance through the presence of the compound, or the physiologically acceptable salt thereof, in the mammal.

6. The method according to claim 5, wherein the physiologically active retinoid is retinoic acid which inherently exist in the living body of said mammal.

7. A compound or a salt thereof represent by the following formula (I):

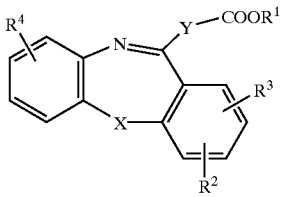

wherein, $R^1$ represents hydrogen atom or a $C_{1-6}$ alkyl group; $R^2$ and $R^3$ independently represent a hydrogen atom or a $C_{1-6}$ alkyl group, or $R^2$ and $R^3$ may combine together with the carbon atoms of the phenyl ring to which $R^2$ and $R^3$ bind to represent a 5- or 6-membered cycloalkyl group which may optionally be substituted with one or more $C_{1-4}$ alkyl groups; $R^4$ represents a hydrogen atom, a $C_{1-6}$ alkyl group, a $C_{1-6}$ alkoxy group, hydroxyl group, nitro group, or a halogen atom; X represents —S—; and Y represents a phenylene group.

8. A pharmaceutical composition comprising a compound of claim 7 or a physiologically accepted salt thereof, and a physiologically acceptable carrier.

9. A method of treatment of a disease selected from the group of vitamin A deficiency disease, hyperkeratosis of epithelial tissue, rheumatism, delayed allergy, and leukemia by enhancing physiological activity of a retinoid, wherein the physiological activity is due to binding of the retinoid to an intranuclear receptor that belongs to the intranuclear receptor super family, the method comprising the step of administering to a mammal a compound of claim 1 or a physiologically acceptable salt thereof.

10. A method according to claim 9, further comprising the step of administering a retinoid.

11. A method of treatment of a disease selected from the group of vitamin A deficiency disease, hyperkeratosis of epithelial tissue, rheumatism, delayed allergy, and leukemia by enhancing physiological activity of a retinoid, wherein the physiological activity is due to binding of the retinoid to an intranuclear receptor that belongs to the intranuclear receptor super family, the method comprising the step of administering to a mammal a compound of claim 7 or a physiologically acceptable salt thereof.

12. A method according to claim 11, further comprising the step of administering a retinoid.

* * * * *